United States Patent
Miller et al.

(10) Patent No.: US 9,603,599 B2
(45) Date of Patent: Mar. 28, 2017

(54) FEATURE TO REENGAGE SAFETY SWITCH OF TISSUE STAPLER

(75) Inventors: Christopher C. Miller, Loveland, OH (US); Edward G. Chekan, Cincinnati, OH (US); Johnny H. Alexander, III, West Chester, OH (US); John F. Cummings, Madeira, OH (US); Carl J. Shurtleff, Mason, OH (US); Adam R. Dunki-Jacobs, Cincinnati, OH (US); Barry T. Jamison, Fairfield, OH (US); Joseph E. Young, Loveland, OH (US); Cortney E. Henderson, Loveland, OH (US)

(73) Assignee: Ethicon Endo-Surgery, LLC, Guaynabo, PR (US)

(*) Notice: Subject to any disclaimer, the term of this patent is extended or adjusted under 35 U.S.C. 154(b) by 1039 days.

(21) Appl. No.: 13/328,344

(22) Filed: Dec. 16, 2011

(65) Prior Publication Data

US 2013/0153630 A1    Jun. 20, 2013

(51) Int. Cl.
*A61B 17/068* (2006.01)
*A61B 17/115* (2006.01)

(52) U.S. Cl.
CPC ........ *A61B 17/115* (2013.01); *A61B 17/1155* (2013.01)

(58) Field of Classification Search
CPC ............ A61B 17/0644; A61B 17/1155; A61B 17/115; A61B 17/07207; A61B 17/068; A61B 17/072; A61B 17/06469
(Continued)

(56) References Cited

U.S. PATENT DOCUMENTS 4,591,085 A * 5/1986 Di Giovanni ........ A61B 17/072
227/19
4,805,823 A    2/1989 Rothfuss
(Continued)

FOREIGN PATENT DOCUMENTS

| EP | 0 050 553 | 4/1982 |
| EP | 1 611 856 | 1/2006 |
| EP | 2 233 084 | 9/2010 |

OTHER PUBLICATIONS

International Search Report dated Feb. 11, 2013 for Application No. PCT/US2012/068859.
(Continued)

*Primary Examiner* — Michelle Lopez
*Assistant Examiner* — Chinyere Rushing-Tucker
(74) *Attorney, Agent, or Firm* — Frost Brown Todd LLC

(57) ABSTRACT

A surgical instrument includes an anvil selectively coupleable to a stapling head assembly and a trigger operable to fire staples into tissue compressed between the anvil and the stapling head assembly. In some versions, a lockout member may engage a securing feature to prevent actuation of the anvil relative to the stapling head assembly. For instance, a tab may engage a slot on an actuator, a screen door lock may provide frictional resistance or engage teeth on the actuator, a door may actuate into engagement with one or more recesses, geared teeth may mesh with teeth on the actuator, the lockout member may include a ratcheting assembly to engage actuator, and/or a push button may actuate into a recess while disengaging the lockout member. Alternatively, in some versions, the trigger actuation assembly may be disengaged prior to firing. An anvil position indicator may restrict engagement of the trigger actuation assembly.

17 Claims, 27 Drawing Sheets

(58) Field of Classification Search
USPC .. 227/175.1, 175.2, 178.1, 19, 175.4, 176.1, 227/180.1, 182.1, 175.3, 134, 5; 606/219, 606/139
See application file for complete search history.

(56) References Cited

U.S. PATENT DOCUMENTS

| | | | |
|---|---|---|---|
| 5,205,459 A | | 4/1993 | Brinkerhoff et al. |
| 5,271,544 A | | 12/1993 | Fox et al. |
| 5,275,322 A | | 1/1994 | Brinkerhoff et al. |
| 5,285,945 A | | 2/1994 | Brinkerhoff et al. |
| 5,292,053 A | | 3/1994 | Bilotti et al. |
| 5,333,733 A | | 8/1994 | Murata |
| 5,333,773 A | | 8/1994 | Main et al. |
| 5,350,104 A | | 9/1994 | Main et al. |
| 5,415,334 A | | 5/1995 | Williamson, IV et al. |
| 5,465,895 A | | 11/1995 | Knodel et al. |
| 5,533,661 A | | 7/1996 | Main et al. |
| 5,597,107 A | | 1/1997 | Knodel et al. |
| 5,632,432 A | | 5/1997 | Schulze et al. |
| 5,673,840 A | | 10/1997 | Schulze et al. |
| 5,704,534 A | | 1/1998 | Huitema et al. |
| 5,762,255 A | * | 6/1998 | Chrisman et al. ......... 227/175.2 |
| 5,814,055 A | | 9/1998 | Knodel et al. |
| 6,783,524 B2 | | 8/2004 | Anderson et al. |
| 6,978,921 B2 | | 12/2005 | Shelton, IV et al. |
| 7,000,818 B2 | | 2/2006 | Shelton, IV et al. |
| 7,143,923 B2 | | 12/2006 | Shelton, IV et al. |
| 7,303,108 B2 | | 12/2007 | Shelton, IV |
| 7,367,485 B2 | | 5/2008 | Shelton, IV et al. |
| 7,380,695 B2 | | 6/2008 | Doll et al. |
| 7,380,696 B2 | | 6/2008 | Shelton, IV et al. |
| 7,404,508 B2 | | 7/2008 | Smith et al. |
| 7,434,715 B2 | | 10/2008 | Shelton, IV et al. |
| 7,721,930 B2 | | 5/2010 | McKenna et al. |
| 8,485,412 B2 | | 7/2013 | Shelton, IV et al. |
| 2005/0015103 A1 | * | 1/2005 | Popov .................. A61B 17/115 606/153 |
| 2005/0023325 A1 | * | 2/2005 | Gresham ............. A61B 17/115 227/176.1 |
| 2005/0070925 A1 | * | 3/2005 | Shelton et al. ............... 606/142 |
| 2005/0116009 A1 | * | 6/2005 | Milliman ............ A61B 17/068 227/176.1 |
| 2006/0097025 A1 | * | 5/2006 | Milliman ............ A61B 17/115 227/175.1 |
| 2010/0072251 A1 | * | 3/2010 | Baxter et al. ............. 227/175.2 |
| 2010/0089971 A1 | * | 4/2010 | Milliman ................ A61B 1/31 227/175.1 |
| 2010/0237132 A1 | * | 9/2010 | Measamer et al. ........ 227/180.1 |
| 2011/0006100 A1 | * | 1/2011 | Milliam .................... 227/175.2 |
| 2013/0116710 A1 | * | 5/2013 | Ziniti et al. .................. 606/144 |
| 2013/0175320 A1 | * | 7/2013 | Mandakolathur .... A61B 17/072 227/175.2 |
| 2013/0284792 A1 | * | 10/2013 | Ma ......................... A61B 1/04 227/176.1 |

OTHER PUBLICATIONS

International Preliminary Report on Patentability dated Jun. 17, 2014 for Application No. PCT/US2012/068859.
Chinese Office Action dated Dec. 28, 2015 for Application No. 201280061751.3, 8 pages.
Partial European Search Report dated May 3, 2016 for Application No. 15188530.8, 8 pages.
Extended European Search Report dated Sep. 2, 2016 for Application No. 15188530.8, 11 pages.

* cited by examiner

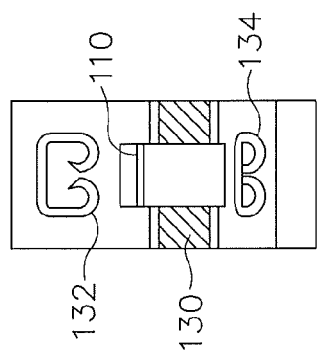
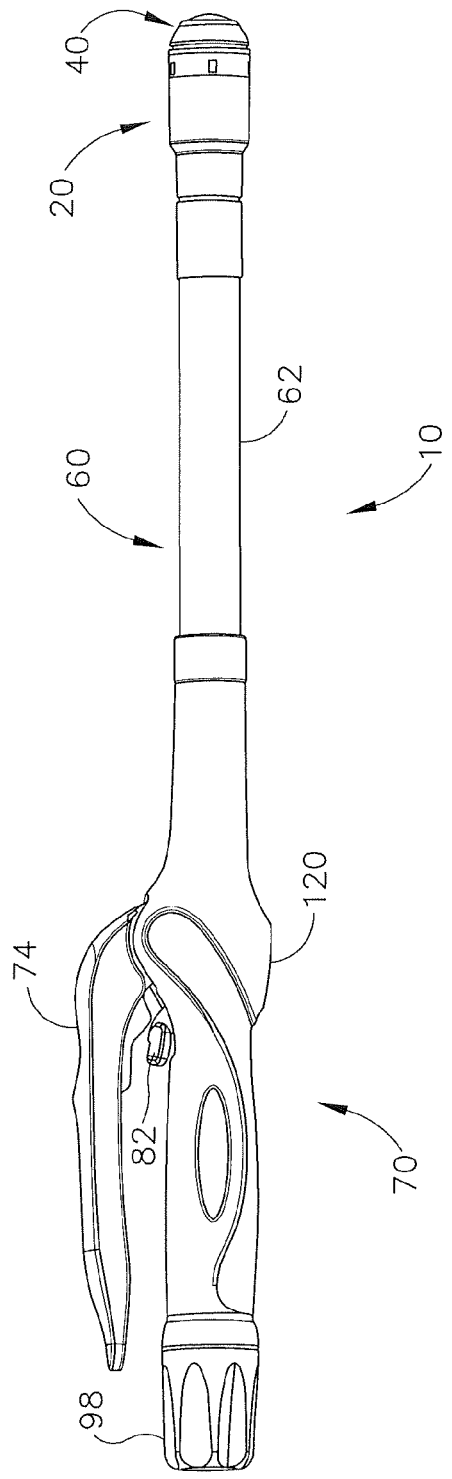

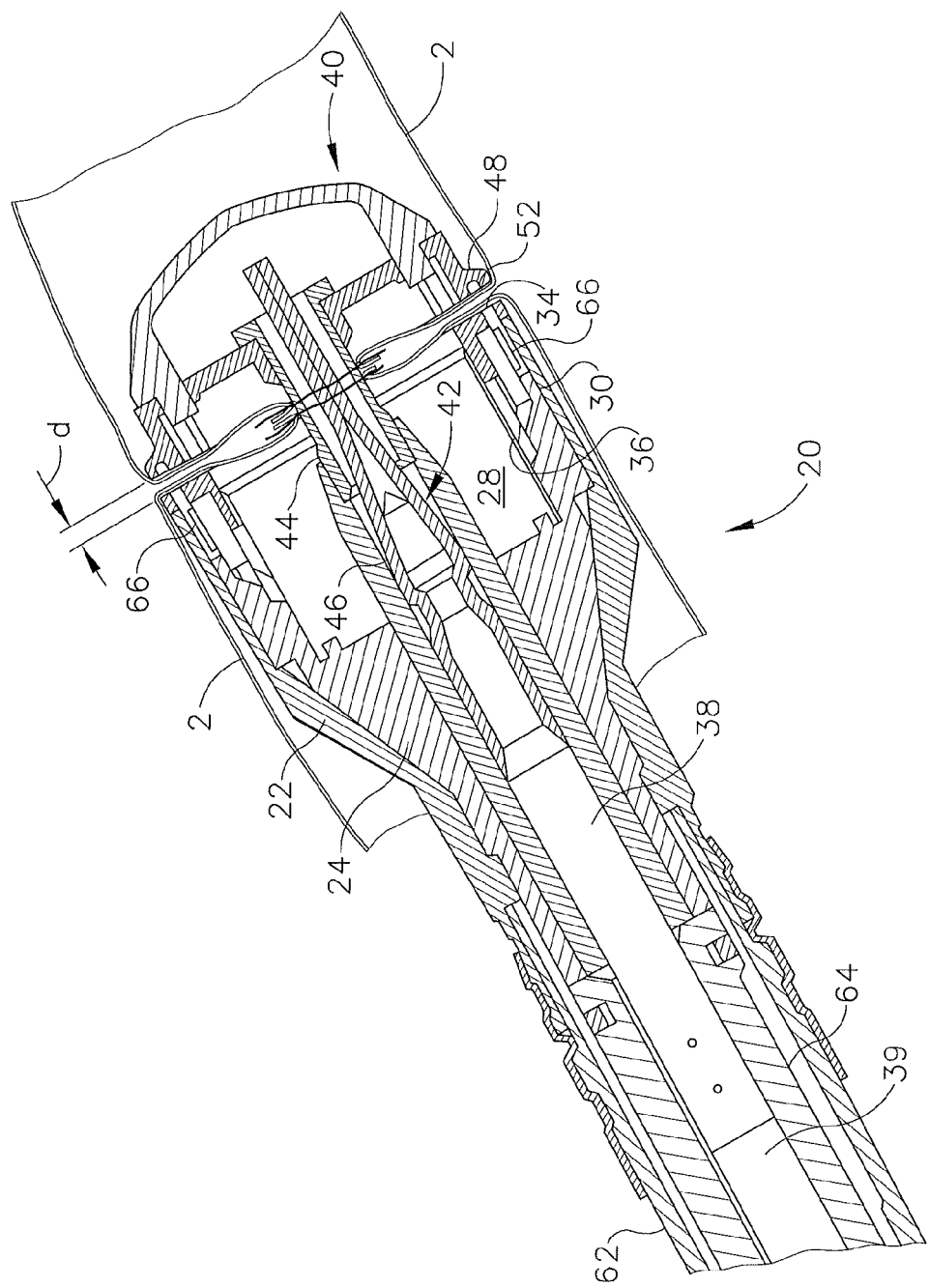

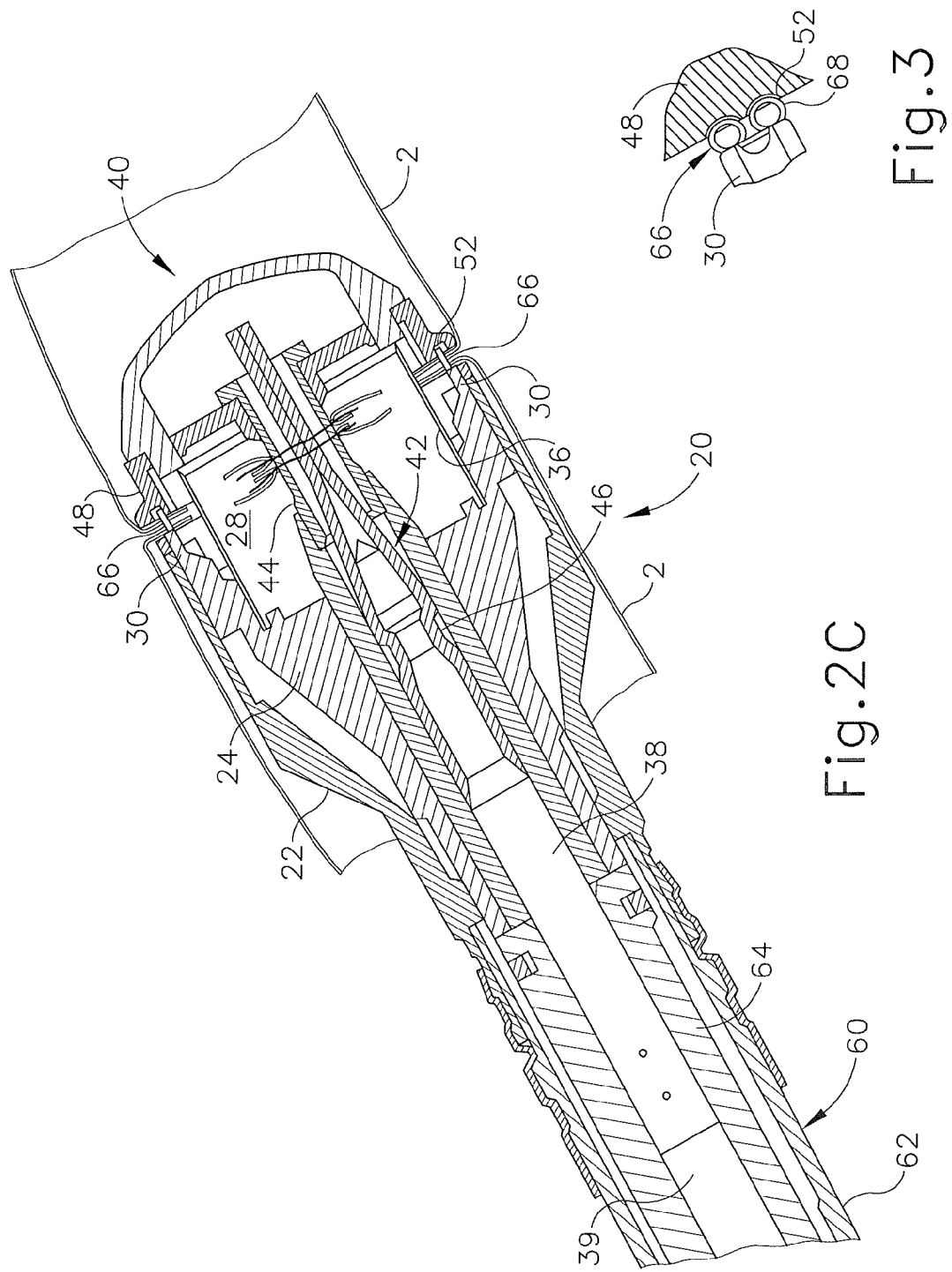

FEATURE TO REENGAGE SAFETY SWITCH OF TISSUE STAPLER

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions will need to be recoupled together. One such tool for accomplishing these anastomotic procedures is a circular stapler that is inserted through a patient's orifice.

Examples of such circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a side elevation view of an exemplary circular stapling surgical instrument;

FIG. 2B depicts an enlarged longitudinal cross-sectional view of the stapling head assembly of FIG. 2A showing the anvil in a closed position;

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 6 depicts an diagrammatic view of the indicator window of FIG. 5 showing an exemplary indicator bar and exemplary corresponding staple representations;

Figure 2A:
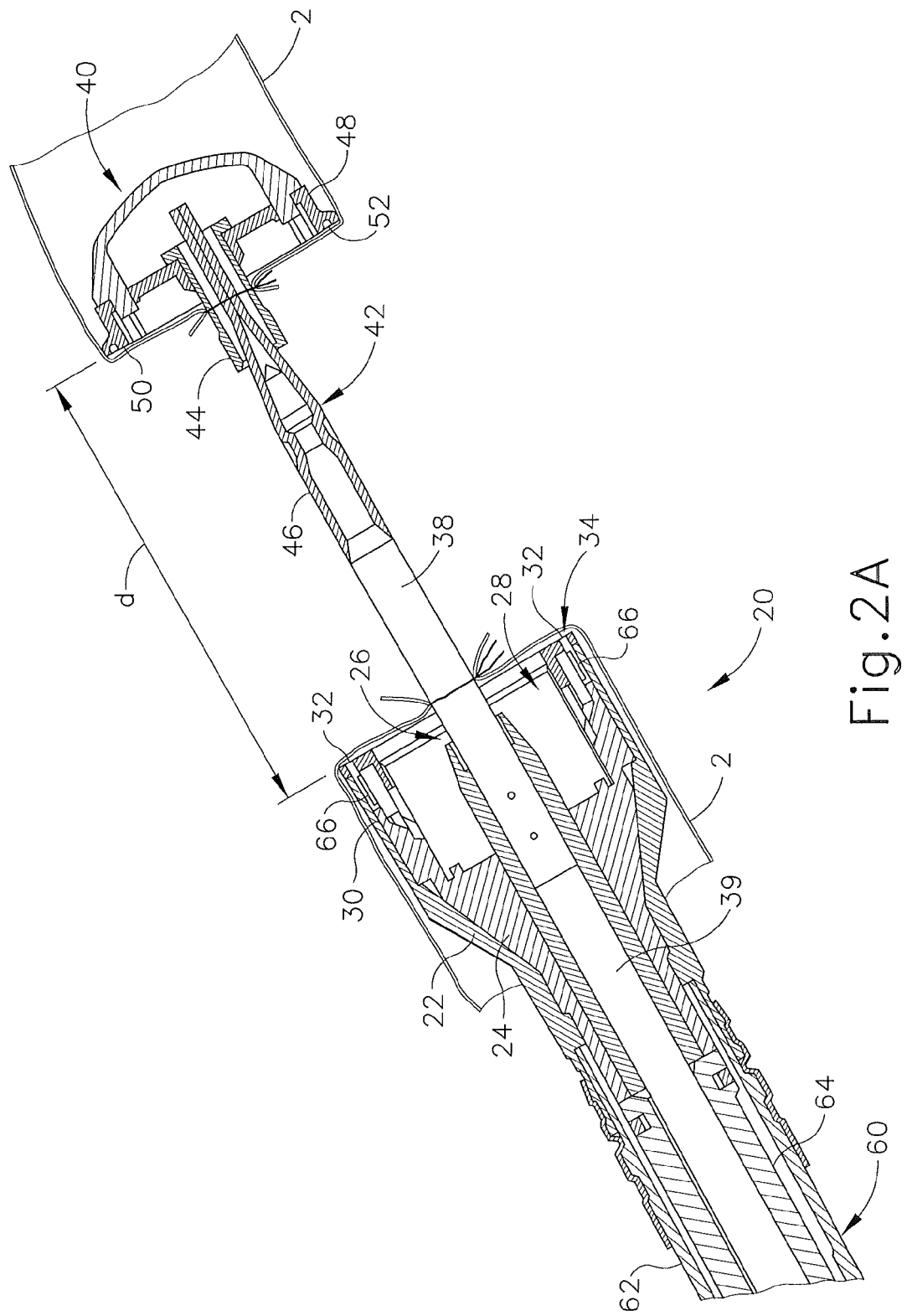
FIG. 2A depicts an enlarged longitudinal cross-section view of an exemplary stapling head assembly of the instrument of FIG. 1 showing an exemplary anvil in an open position.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples. It should be understood that staple forming pockets (52) are merely optional and may be omitted in some versions.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

Figure 5:
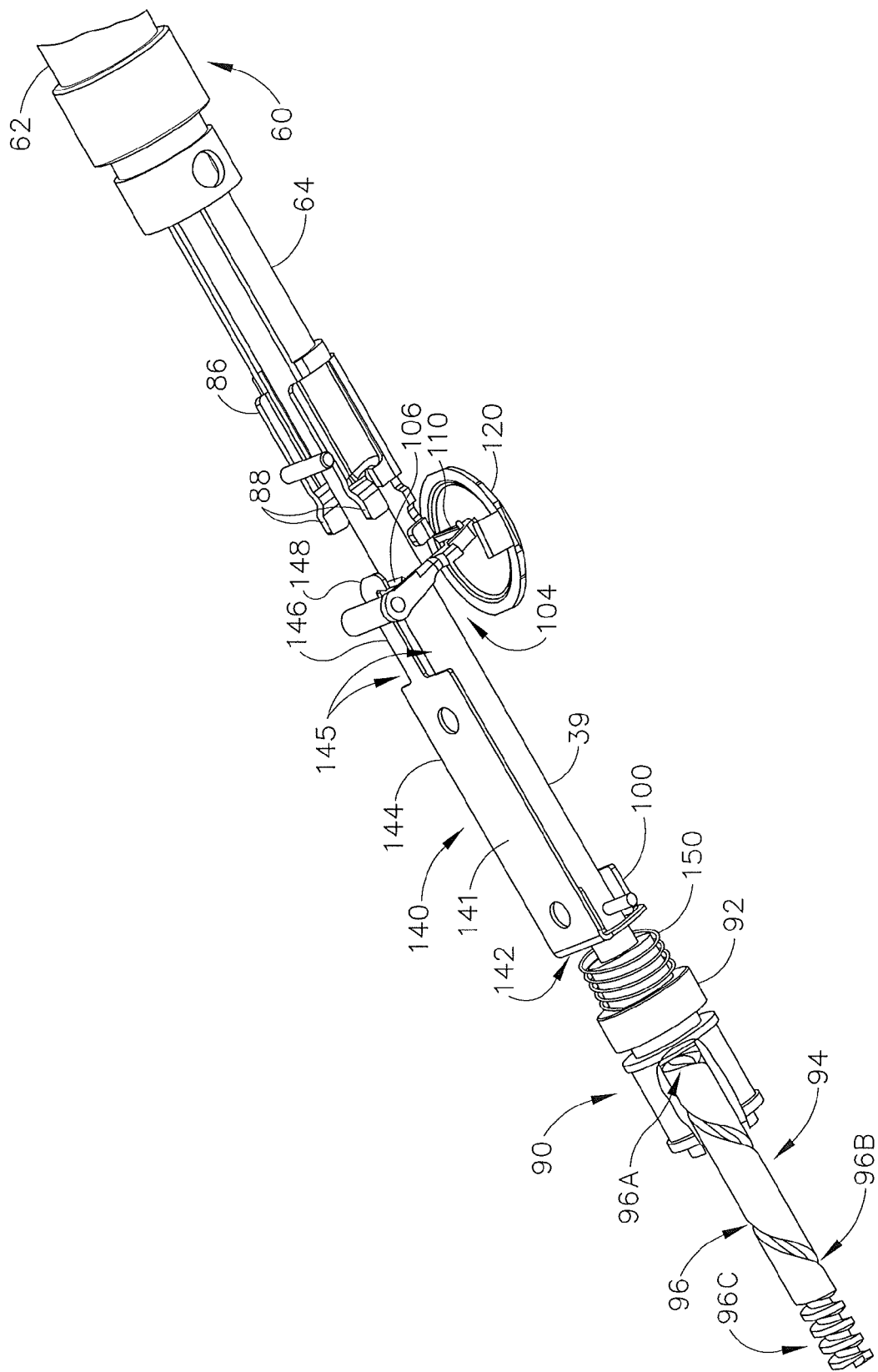
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32).

Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

D. Exemplary Actuator Handle Assembly

Figure 4A:
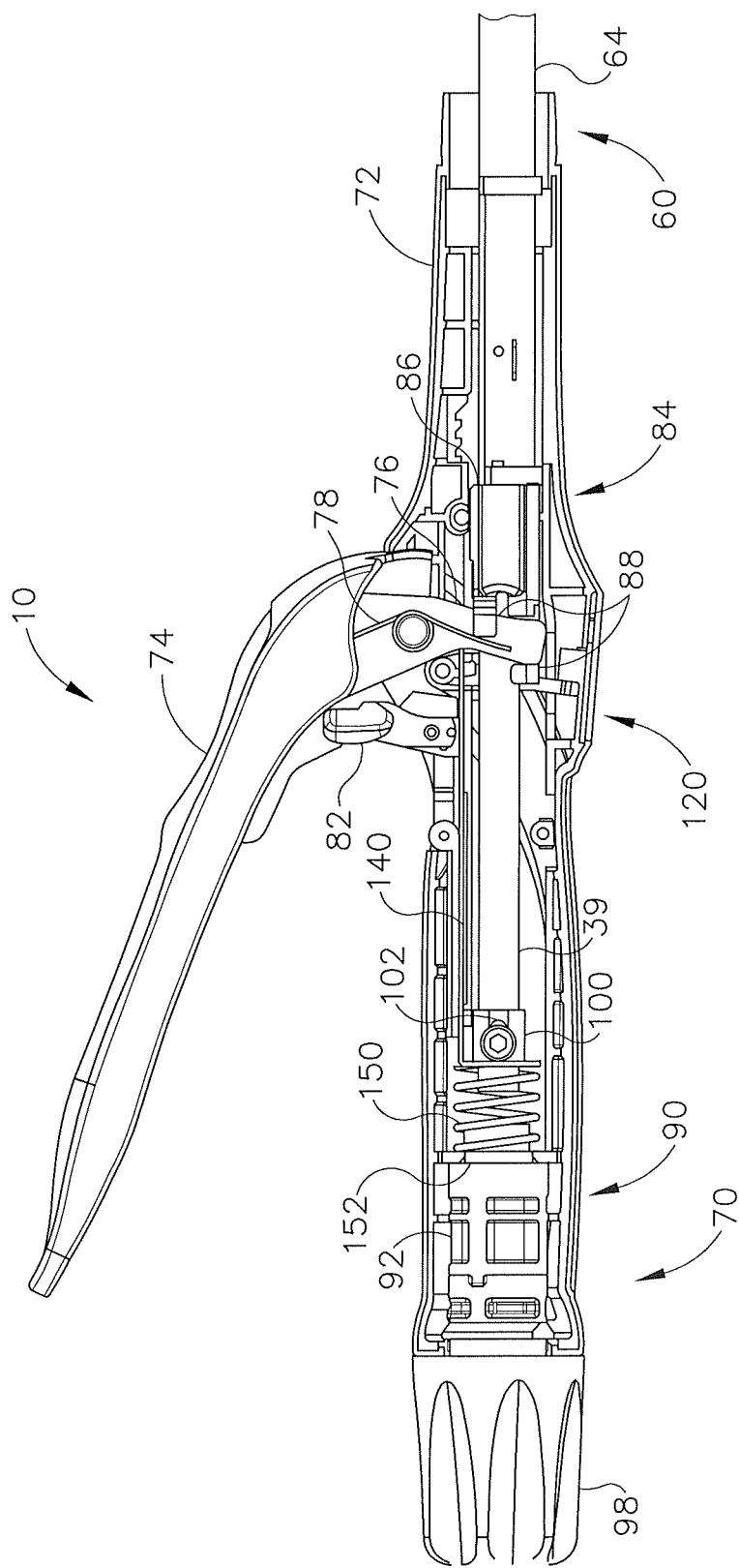
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
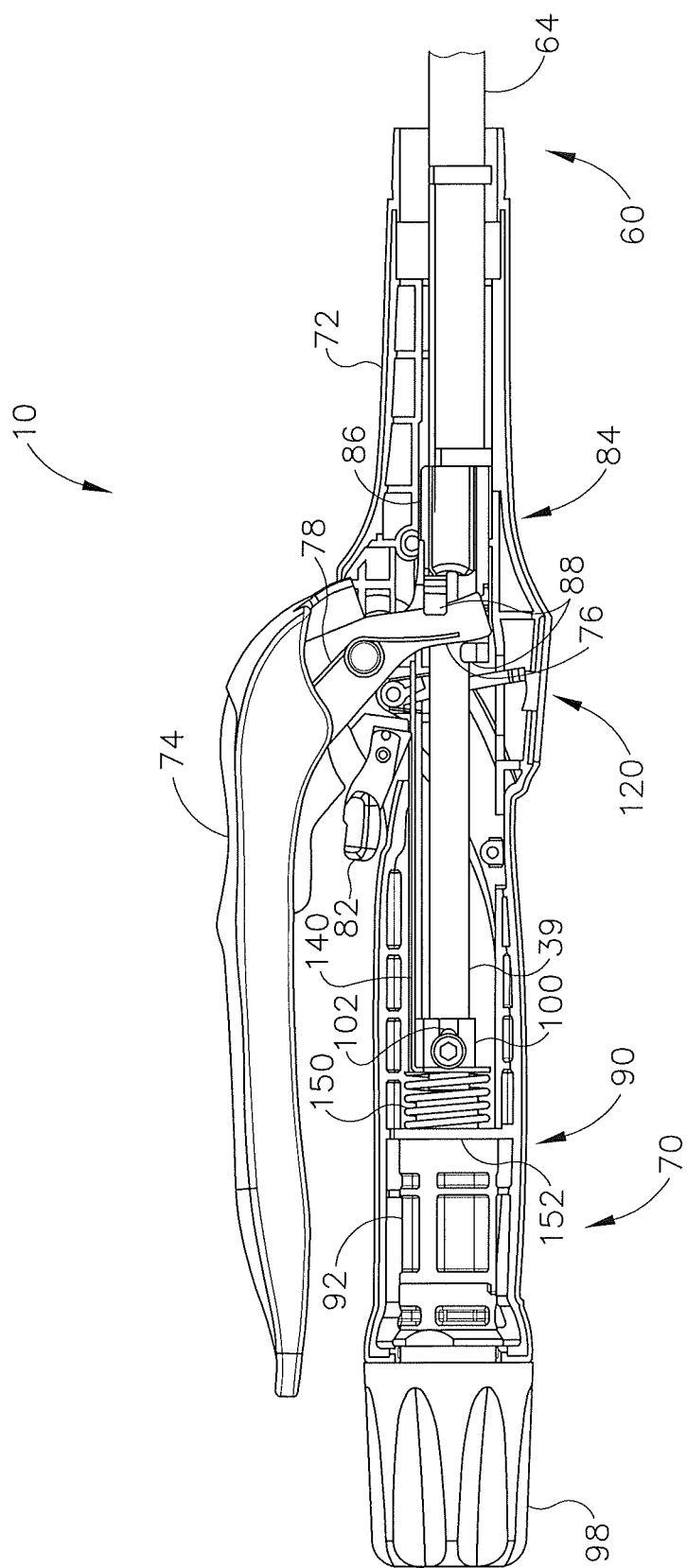
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72) and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). U-shaped clip (100) engages with a portion of body (72) to substantially prevent trocar actuator (39) from rotating about its axis when adjusting knob (98) is rotated. U-shaped clip (100) further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104).

Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

II. Exemplary Trocar Actuator Locking Assemblies

In some instances, it may be useful to a user to lock trocar actuator (39) in position once lockout feature (82) is disengaged. For instance, some users may inadvertently twist adjusting knob (98) when pulling trigger (74). Twisting adjusting knob (98) may result in anvil (40) actuating proximally or distally from a desired position relative to stapling head assembly (20). Accordingly, the staple size may become too small or too large, or, in some instances, anvil (40) may be actuated such that incomplete stapling of staples (66) occurs (i.e., anvil (40) is no longer in the "green zone"). Accordingly, securing trocar actuator (39) from actuating proximally or distally once lockout feature (82) is disengaged may reduce the likelihood of such occurrences.

A. Exemplary Spring-Loaded Brake

Figure 7A:
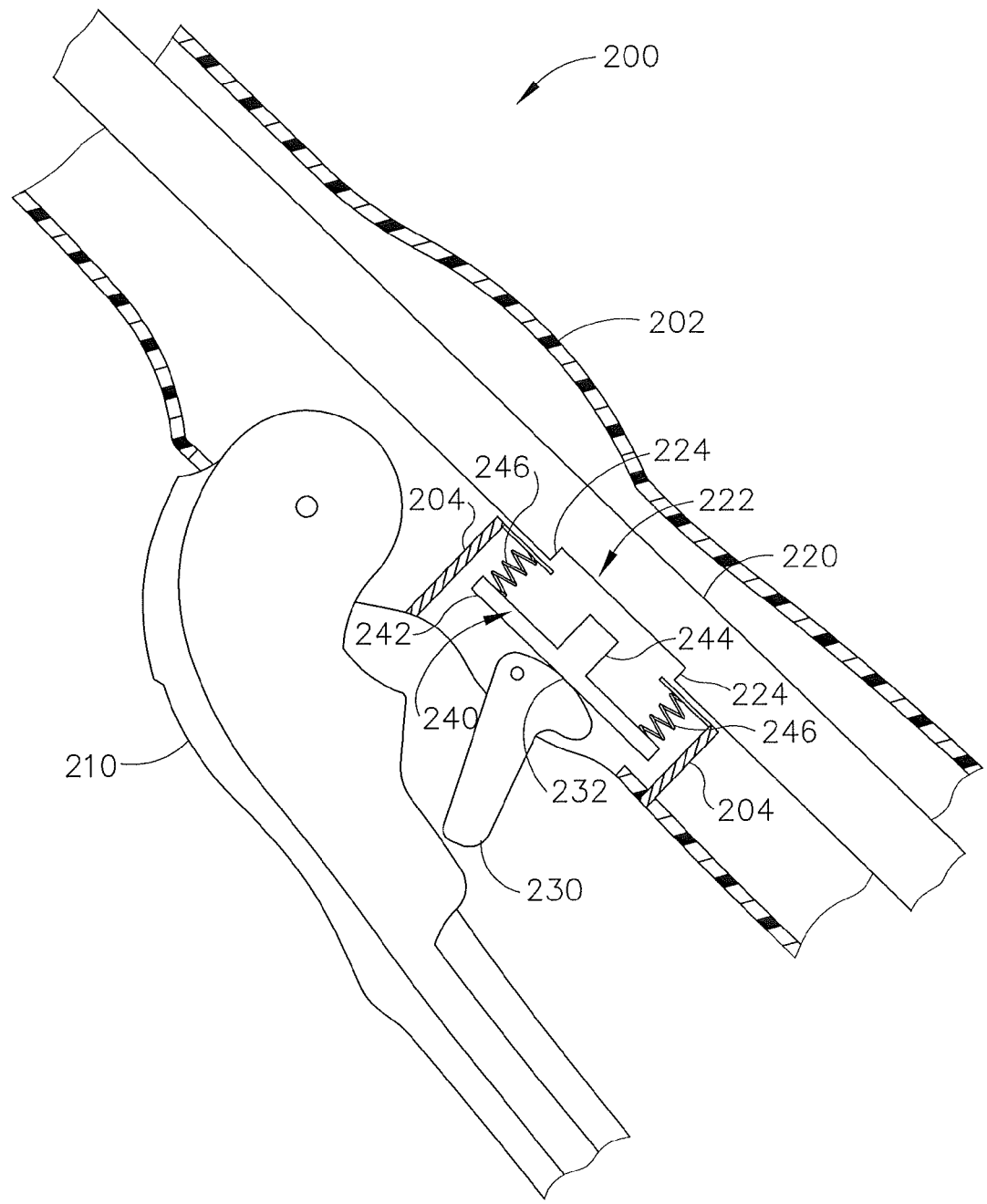
FIG. 7A depicts a partial side cross-sectional view of an exemplary spring-loaded brake and lockout feature shown in a locked position.
Figure 7B:
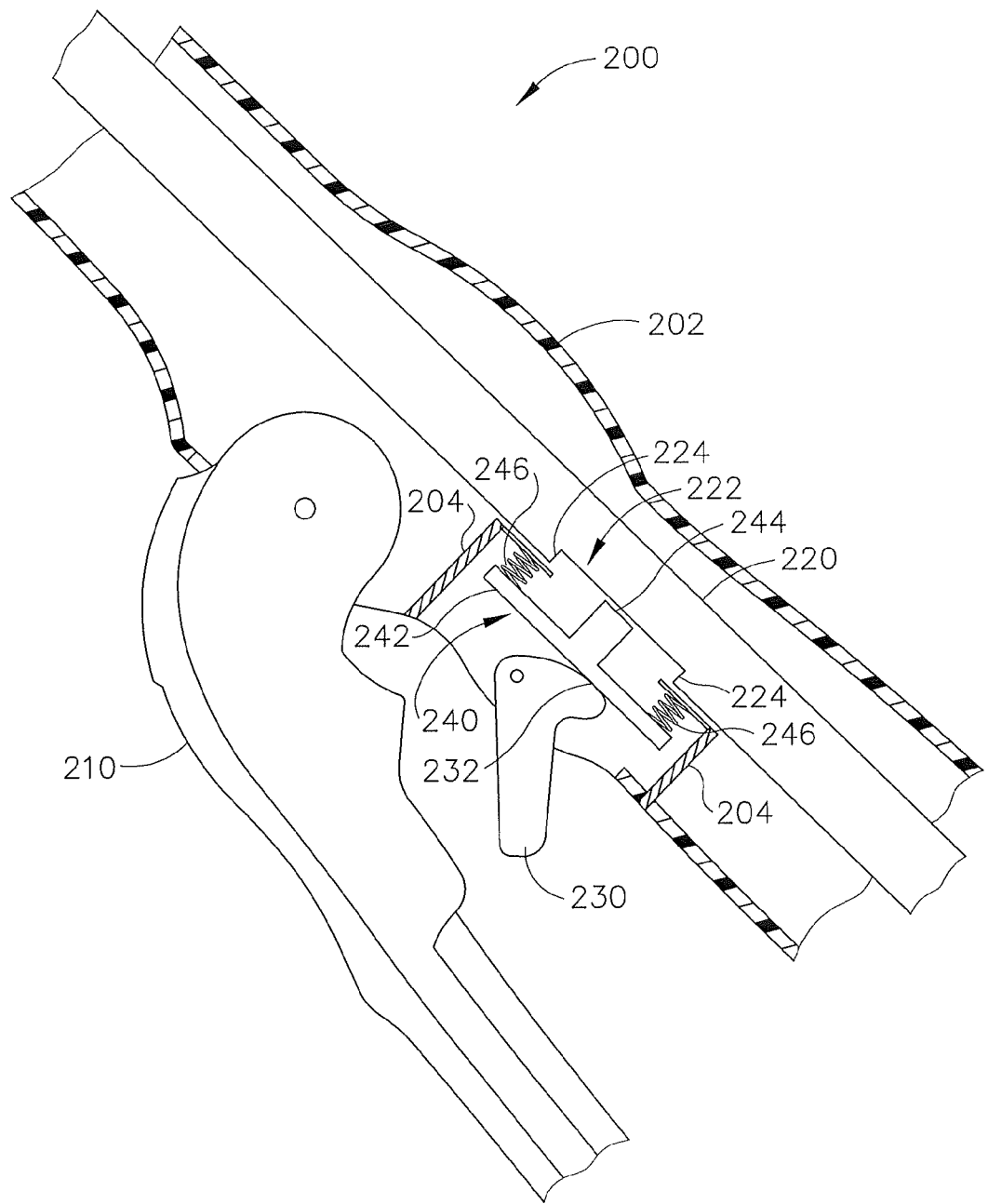
FIG. 7B depicts a partial side cross-sectional view of the spring-loaded brake and lockout feature of FIG. 7A shown in a firing position.

FIGS. 7A-7B depict an exemplary actuator handle assembly (200) for surgical instrument (10), described above, having a body (202), a trigger (210) pivotably mounted to body (202), and a trocar actuator (220) extending longitudinally through body (202). In the present example, trocar actuator (220) is coupled to an anvil (not shown), such as anvil (40), at a distal end. A proximal end of trocar actuator (220) is in communication with an adjusting knob (not shown), such as adjusting knob (98), to actuate trocar actuator (220) proximally and/or distally relative to actuator handle assembly (200). Accordingly, when the anvil is coupled to the distal end of trocar actuator (220) and the adjusting knob is rotated, trocar actuator (220) increases or decreases the distance between the anvil and a stapling head assembly (not shown). Trigger (210) is operable to drive staples (not shown) out of the stapling head assembly and into tissue. Body (202), trigger (210), trocar actuator (220) and/or actuator handle assembly (200) may be further constructed in accordance with at least some of the teachings of body (72), trigger (74), trocar actuator (39), and/or actuator handle assembly (70) described above.

In the example shown, a lockout feature (230) is also pivotably coupled to body (202) and is configured to pivot between a first position shown in FIG. 7A, in which lockout feature (230) is engaged with trigger (210) to substantially prevent trigger (210) from being fired, and a second position shown in FIG. 7B, in which lockout feature (230) is disengaged from trigger (210). Lockout feature (230) may be constructed and/or function at least partially in accordance with lockout feature (82) described above. As shown, lockout feature (230) includes a cam surface (232) that interacts with a spring-loaded brake (240). In some versions, cam surface (232) may comprise a frictional material, such as rubber, that engages brake (240) to resist longitudinal movement of brake (240) relative to cam surface (232). Brake (240) comprises a plate (242) and an engagement feature (244) extending from plate (242). As shown in FIG. 7A, a pair of springs (246) are disposed between plate (242) and bosses (204) of body (202) to bias brake (240) toward cam surface (242). Of course, springs (246) are merely optional and may be omitted. In some versions, lockout feature (230) may include a retention member (not shown) configured to selectively secure lockout feature (230) to body (202) such that lockout feature (230) is not pivoted back to the first position via the bias provided by springs (246). In addition, or in the alternative, brake (240) may be coupled to trocar actuator (220) and plate (242) may extend longitudinally such that lockout feature (230) engages brake (240) at any longitudinal position. Engagement feature (244) of the present example comprises a square tab extending from plate (242) and is configured to selectively enter a notch or recess (222) formed in trocar actuator (220). Of course engagement feature (244) may include other sized tabs, meshing teeth, ratcheting features, and/or any other feature as will be apparent to one of ordinary skill in the art in view of the teachings herein.

Recess (222) has a longitudinal length corresponding to the longitudinal path of trocar actuator (220) when actuated within the "green zone" described above. Accordingly, when engagement feature (244) is inserted into recess (222), trocar actuator (220) is actuatable within the "green zone," but engagement feature (244) abuts an end (224) of recess (222) when either limit of the "green zone" is reached. Of course recess (222) may include a smaller or larger longitudinal length.

FIG. 7A shows lockout feature (230) in the locked position such that trigger (210) is inoperable by the user. Once the user has rotated the adjusting knob to actuate the anvil (and therefore also trocar actuator (220)) into the "green zone," engagement feature (244) is positioned adjacent to at least a portion of recess (222). When lockout feature (230) is pivoted to the second position, shown in FIG. 7B, cam surface (232) engages brake (240) to insert engagement feature (244) into recess (222). As noted above, the user may then actuate trocar actuator (220), but only within the "green zone." If the user attempts to move trocar actuator (220) out of the "green zone" while lockout feature (230) is disengaged, engagement feature (244) is impeded by either end (224) of recess (222). In some versions, recess (222) may be sized such that trocar actuator (220) cannot be longitudinally actuated once lockout feature (230) is disengaged. In addition, or in the alternative, a plurality of small recesses (222) may be disposed along the length of trocar actuator (220) to provide a plurality of locking positions for engagement feature (244). With trocar actuator (220) secured relative to body (202) via brake (240), the user may then fire the instrument to staple the tissue. Of course other configurations for brake (240) and/or lockout feature (230) will be apparent to one of ordinary skill in the art in view of the teachings herein.

B. Exemplary Screen Door Lock

Figure 8A:
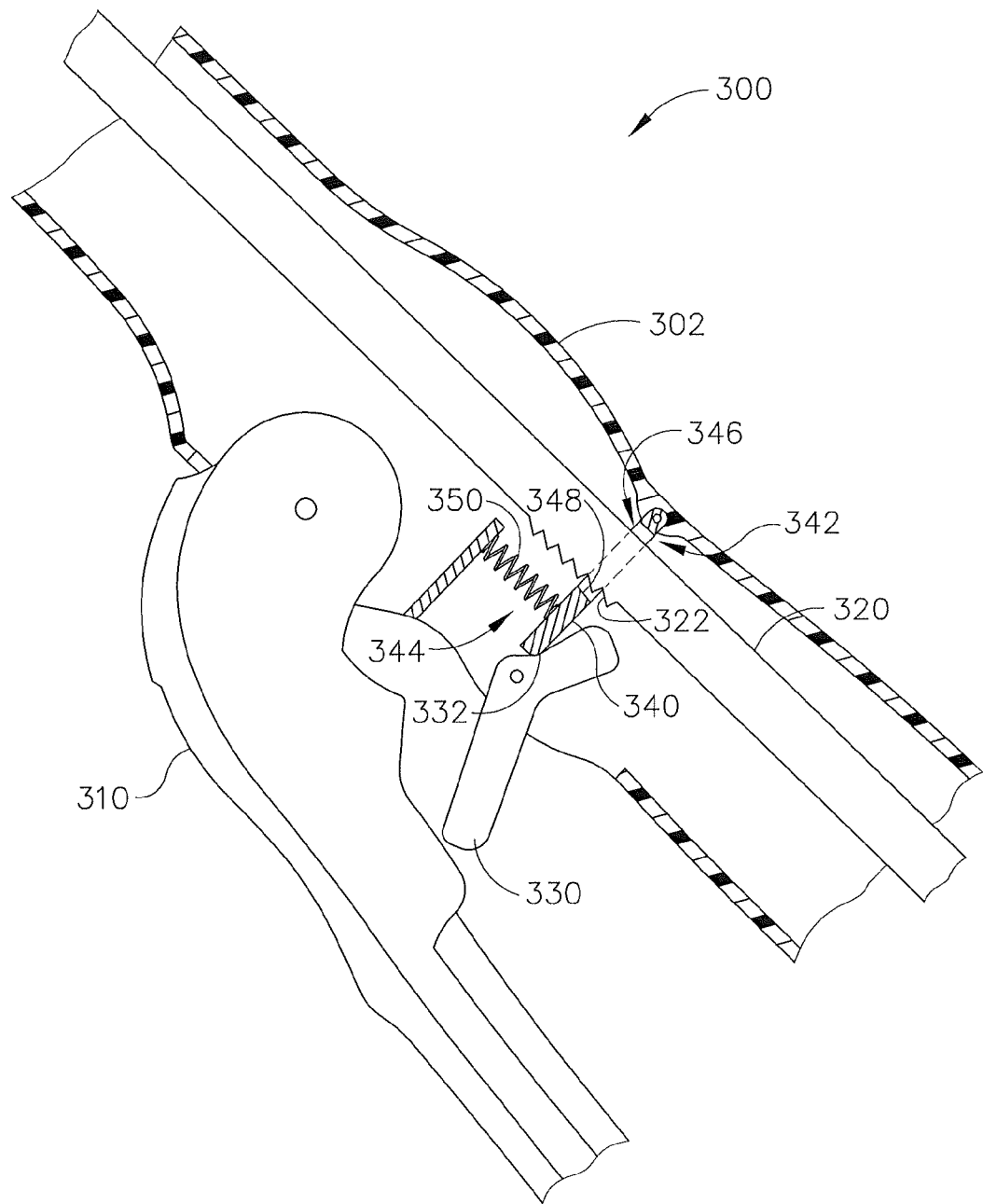
FIG. 8A depicts a partial side cross-sectional view of an exemplary screen door lock and lockout feature shown in a locked position.
Figure 8B:
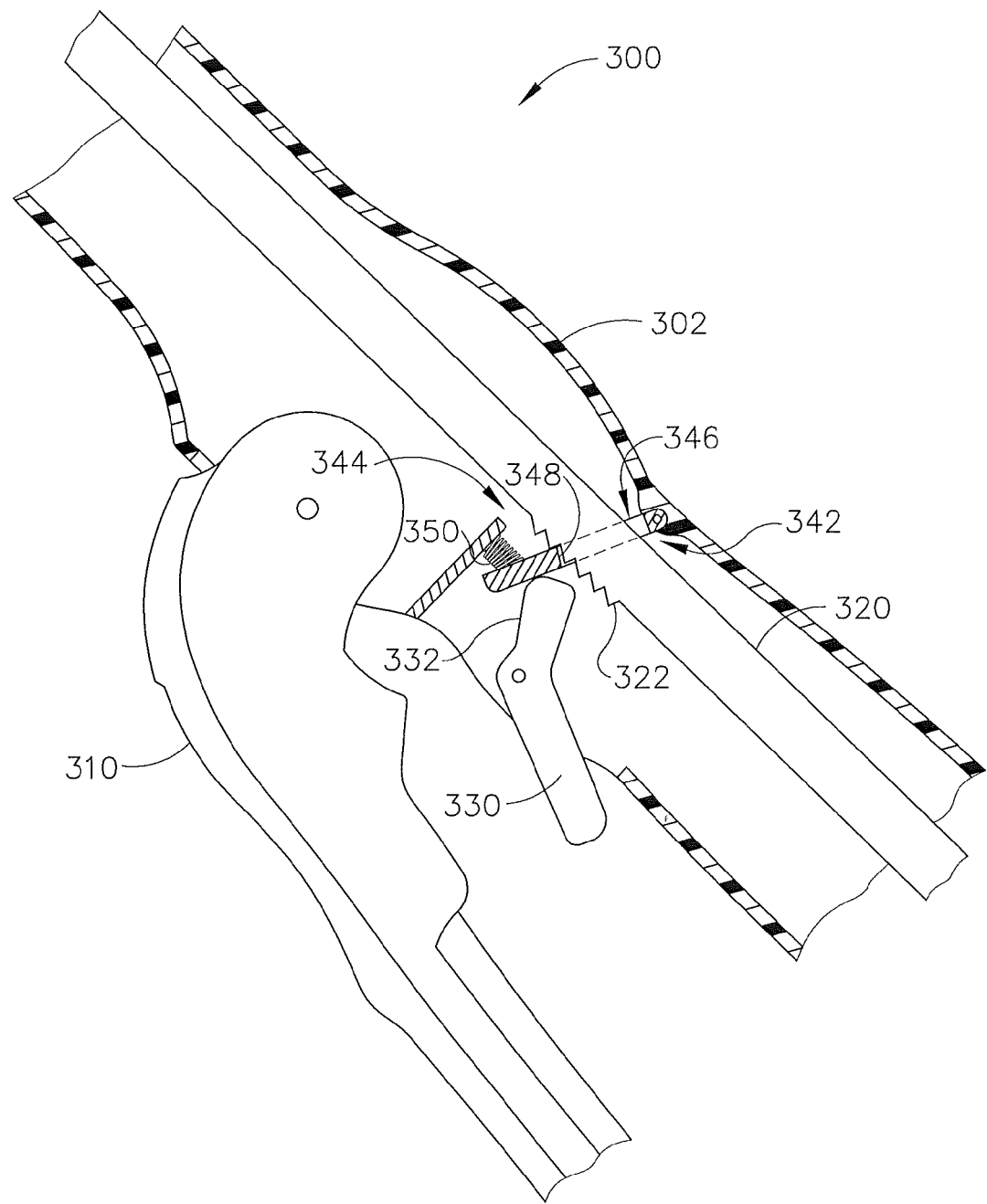
FIG. 8B depicts a partial side cross-sectional view of the screen door lock and lockout feature of FIG. 8A shown in a firing position.

FIGS. 8A-8B depict an exemplary actuator handle assembly (300) for surgical instrument (10), described above, having a body (302), a trigger (310) pivotably mounted to body (302), and a trocar actuator (320) extending longitudinally through body (302). In the present example, trocar actuator (320) is coupled to an anvil (not shown), such as anvil (40), at a distal end. A proximal end of trocar actuator (320) is in communication with an adjusting knob (not shown), such as adjusting knob (98), to actuate trocar actuator (320) proximally and/or distally relative to actuator handle assembly (300). Accordingly, when the anvil is coupled to the distal end of trocar actuator (320) and the adjusting knob is rotated, trocar actuator (320) increases or decreases the distance between the anvil and a stapling head assembly (not shown). Trigger (310) is operable to drive staples (not shown) out of the stapling head assembly and into tissue. Body (302), trigger (310), trocar actuator (320) and/or actuator handle assembly (300) may be further constructed in accordance with at least some of the teachings of body (72), trigger (74), trocar actuator (39), and/or actuator handle assembly (70) described above.

In the example shown, a lockout feature (330) is also pivotably coupled to body (302) and is configured to pivot between a first position shown in FIG. 8A, in which lockout feature (330) is engaged with trigger (310) to substantially prevent trigger (310) from being fired, and a second position shown in FIG. 8B, in which lockout feature (330) is disengaged from trigger (310). Lockout feature (330) may be constructed and/or function at least partially in accordance with lockout feature (82) described above. As shown, lockout feature (330) includes a cam surface (332) that interacts with a screen door lock (340). Screen door lock (340) is pivotably coupled to body (302) at a first end (342). A second end (344) of screen door lock (340) is coupled to a spring (350) that is also coupled to a portion of body (302). Spring (350) of the present example is a compression spring configured to bias second end (344) into cam surface (332). In some versions, lockout feature (330) may include a retention member (not shown) configured to selectively secure lockout feature (330) to body (302) such that lockout feature (330) is not pivoted back to the first position via the bias provided by spring (350). Of course, it should be understood that spring (350) may be omitted and screen door lock (340) may be linked or otherwise coupled to lockout feature (340).

In the present example, screen door lock (340) also includes an opening (346) formed therethrough and comprises an edge (348) configured to engage one or more teeth (322) formed on an outer portion of trocar actuator (320). In some versions, edge (348) may include a frictional material, such as rubber, configured to frictionally resist movement of trocar actuator (320). In the present example, trocar actuator (320) extends through and is longitudinally actuatable relative to opening (346). As shown, a plurality of teeth (322) are formed on the exterior of trocar actuator (320), though it should be understood that a plurality of notches may be formed in trocar actuator (320) and/or a single tooth or notch may be provided for edge (348) to lock into. Of course still further configurations of screen door lock (340) and/or trocar actuator (320) will be apparent to one of ordinary skill in the art in view of the teachings herein.

FIG. 8A shows lockout feature (330) in the locked position such that trigger (310) is inoperable by the user. In this position, the user can rotate the adjusting knob to actuate the anvil (and therefore also trocar actuator (320)) into the "green zone." With screen door lock (340) shown in a first position with edge (348) not engaged with teeth (322), trocar actuator (320) can move longitudinally through opening (346) in response to a rotation of the adjusting knob. Accordingly, the user may adjust to position of the anvil relative to the stapling head assembly. When lockout feature (330) is pivoted to the second position, shown in FIG. 8B, cam surface (332) engages and pivots screen door lock (340) to its second position. When screen door lock (340) is pivoted to the second position, edge (348) engages with teeth (322) and screen door lock (340) substantially prevents trocar actuator (320) from actuating longitudinally. Thus, if a user inadvertently exerts a rotational force on the adjusting knob, screen door lock (340) maintains the position of trocar actuator (320) and the anvil relative to the stapling head assembly. With trocar actuator (320) secured relative to body (302) via screen door lock (340), the user may then fire the instrument to staple the tissue. Yet other configurations for screen door lock (340) and/or lockout feature (330) will be apparent to one of ordinary skill in the art in view of the teachings herein.

C. Exemplary Lockout Feature with Brake

Figure 9A:
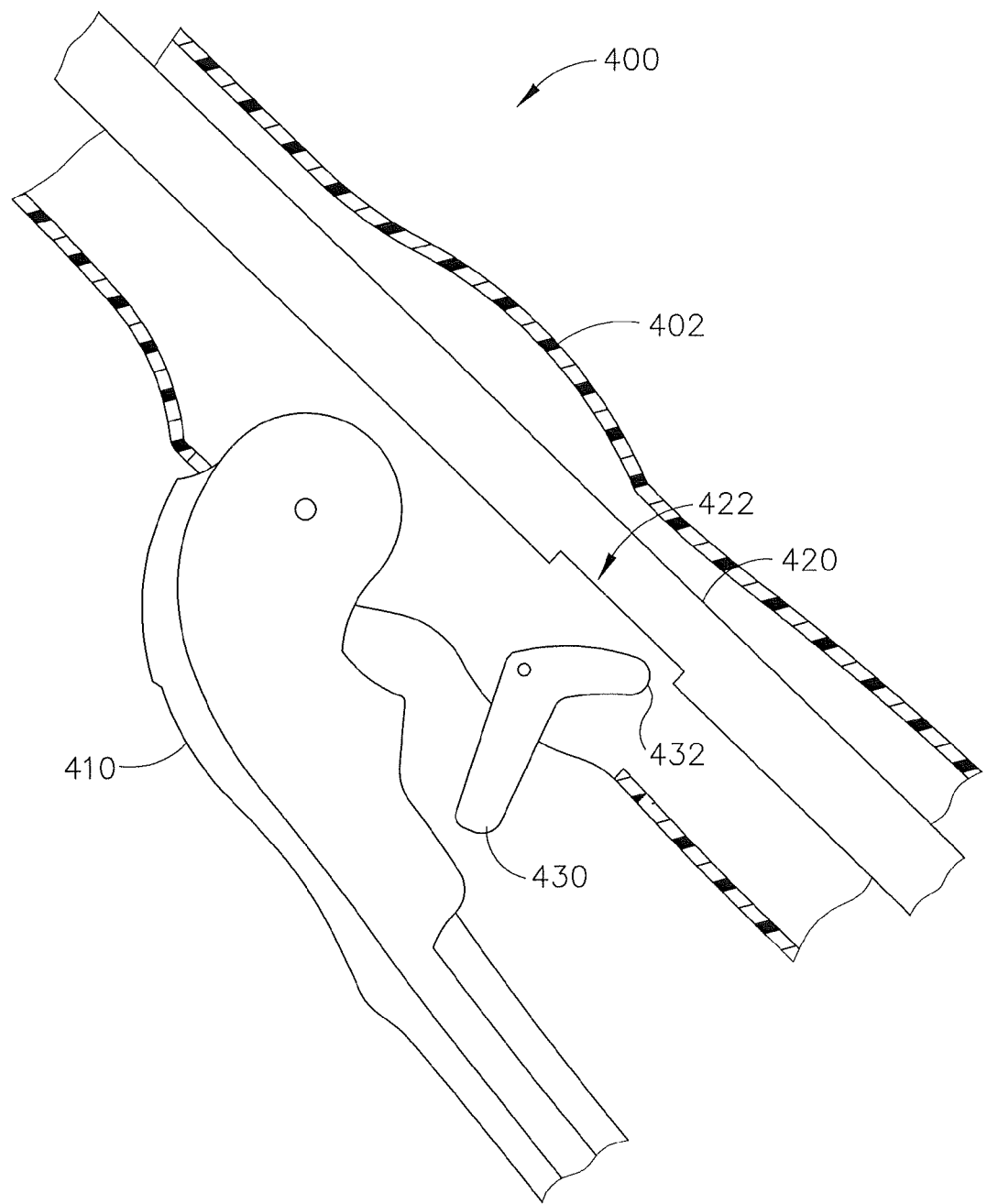
FIG. 9A depicts a partial side cross-sectional view of an exemplary lockout feature having a brake shown in a locked position.
Figure 9B:
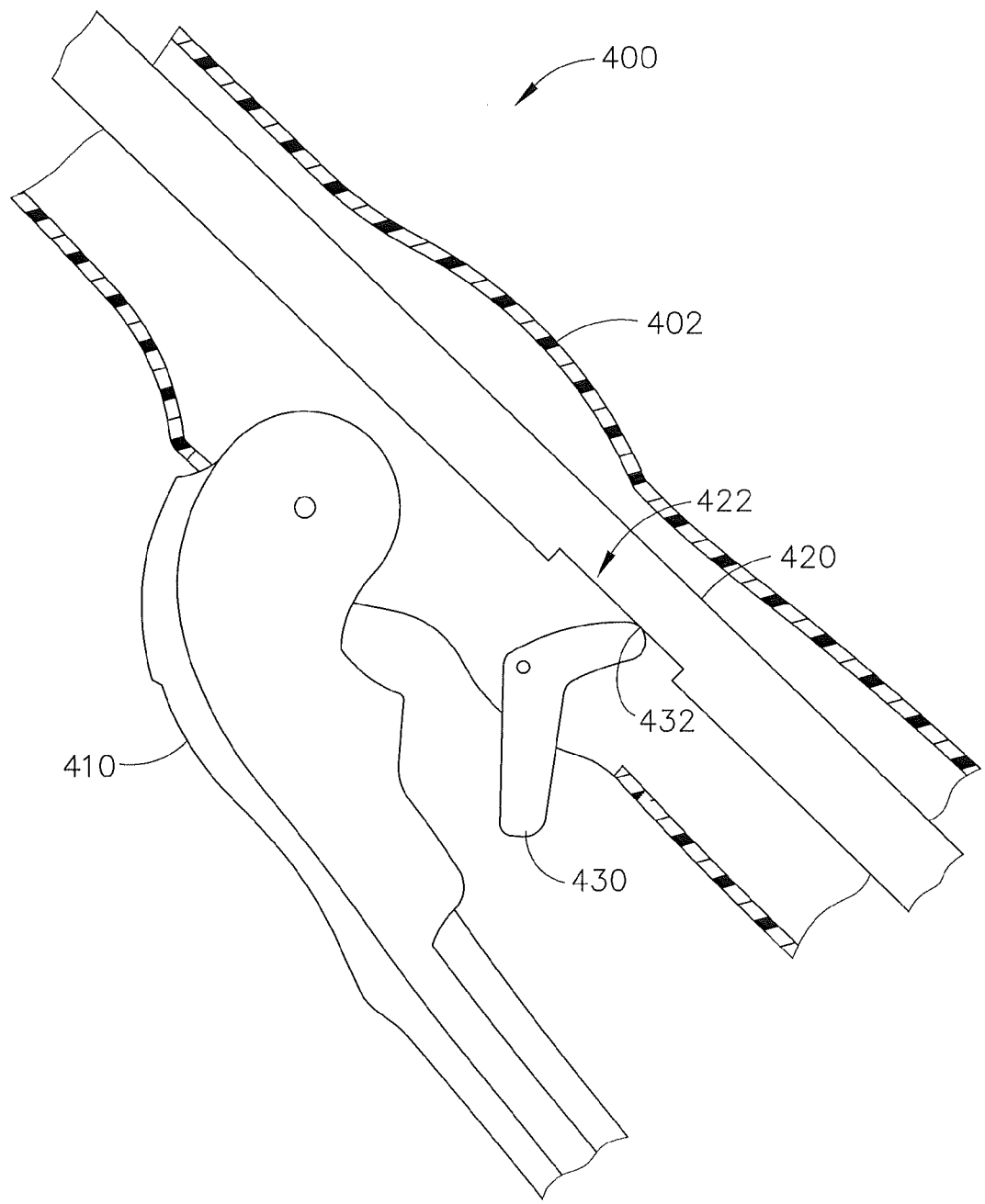
FIG. 9B depicts a partial side cross-sectional view of the lockout feature of FIG. 9A shown in a firing position.

FIGS. 9A-9B depict an exemplary actuator handle assembly (400) for surgical instrument (10), described above, having a body (402), a trigger (410) pivotably mounted to body (402), and a trocar actuator (420) extending longitudinally through body (402). In the present example, trocar actuator (420) is coupled to an anvil (not shown), such as anvil (40), at a distal end. A proximal end of trocar actuator (420) is in communication with an adjusting knob (not shown), such as adjusting knob (98), to actuate trocar actuator (420) proximally and/or distally relative to actuator handle assembly (400). Accordingly, when the anvil is coupled to the distal end of trocar actuator (420) and the adjusting knob is rotated, trocar actuator (420) increases or decreases the distance between the anvil and a stapling head assembly (not shown). Trigger (410) is operable to drive staples (not shown) out of the stapling head assembly and into tissue. Body (402), trigger (410), trocar actuator (420) and/or actuator handle assembly (400) may be further constructed in accordance with at least some of the teachings of body (72), trigger (74), trocar actuator (39), and/or actuator handle assembly (70) described above.

In the example shown, a lockout feature (430) is also pivotably coupled to body (402) and is configured to pivot between a first position shown in FIG. 9A, in which lockout feature (430) is engaged with trigger (410) to substantially prevent trigger (410) from being fired, and a second position shown in FIG. 9B, in which lockout feature (430) is disengaged from trigger (410). Lockout feature (430) may be constructed and/or function at least partially in accordance with lockout feature (82) described above. Lockout feature (430) further includes a cam surface (432) that engages with a portion of trocar actuator (420) to substantially prevent trocar actuator (420) from actuating longitudinally. As shown, cam surface (432) enters into a recess (422) formed in trocar actuator (420), though this is merely optional. In some instances, cam surface (432) may directly engage an outer surface of trocar actuator (420). Referring back to the present example, recess (422) is positioned such that lockout feature (430) is pivotable from the locked position only when trocar actuator (420) and the anvil are in a position corresponding to the "green zone." When lockout feature (430) is pivoted, a frictional material, such as rubber, of cam surface (432) engages with a surface of trocar actuator (420) to frictionally resist movement of trocar actuator (420). In some versions, lockout feature (430) may include a retention member (not shown) configured to selectively secure lockout feature (420) to body (402) such that lockout feature (430) is not pivoted back to the first position if trocar actuator is moved.

FIG. 9A shows lockout feature (430) in the locked position such that trigger (410) is inoperable by the user. Once the user has rotated the adjusting knob to actuate the anvil (and therefore also trocar actuator (420)) into the "green zone," at least a portion of recess (422) is aligned with lockout feature (430). When lockout feature (430) is pivoted to the second position, shown in FIG. 9B, cam surface (432) engages recess (422) to frictionally resist movement of trocar actuator (420). Thus, if a user inadvertently applies a rotational force on the adjusting knob, cam surface (432) frictionally maintains the position of trocar actuator (420) and the anvil relative to the stapling head assembly. With trocar actuator (420) secured relative to body (402) via cam surface (432), the user may then fire the instrument to staple the tissue. Still other configurations for trocar actuator (420) and/or lockout feature (430) will be apparent to one of ordinary skill in the art in view of the teachings herein.

D. Exemplary Trapdoor Assembly

Figure 10A:
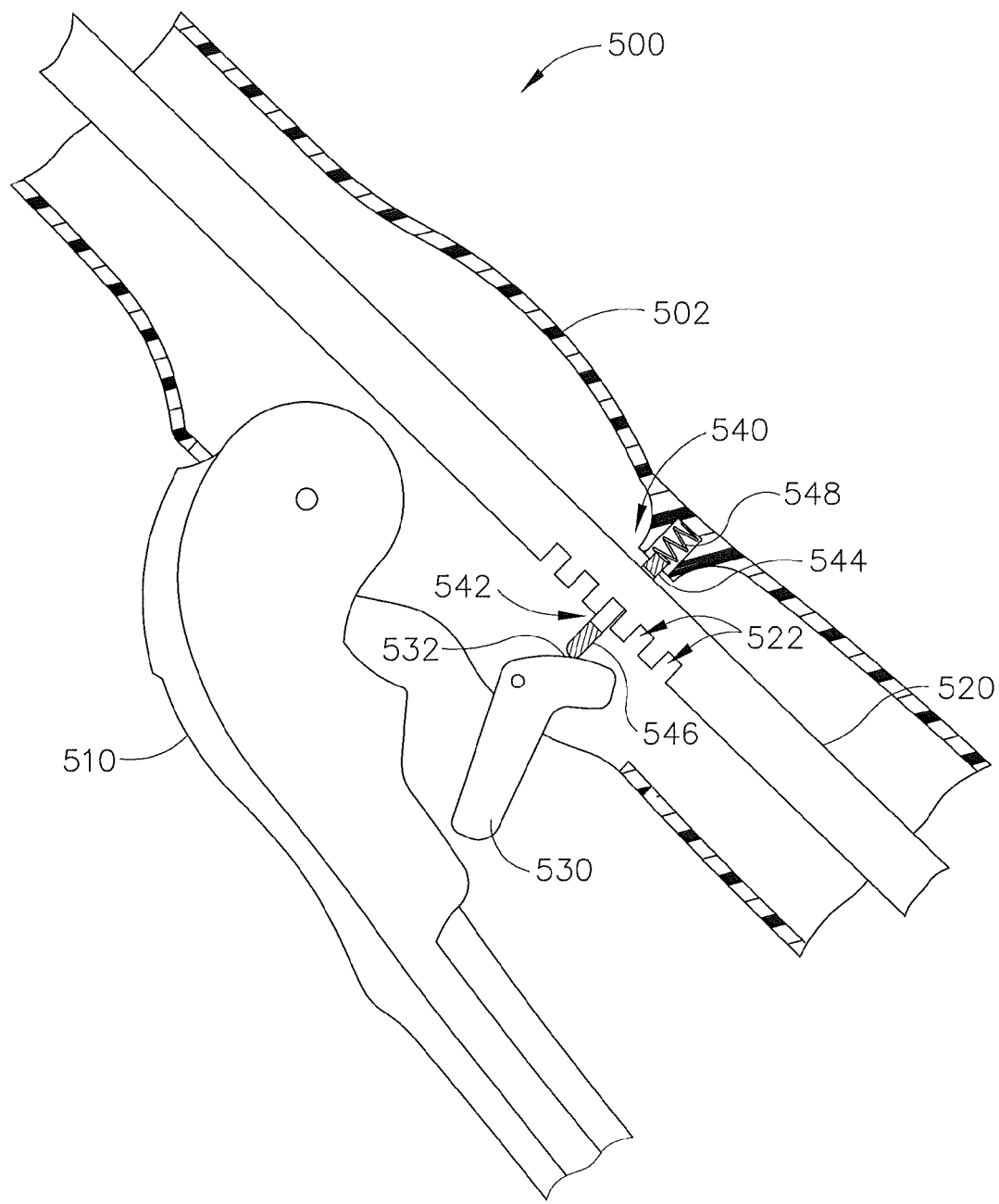
FIG. 10A depicts a partial side cross-sectional view of an exemplary trapdoor and lockout feature shown in a locked position.
Figure 10B:
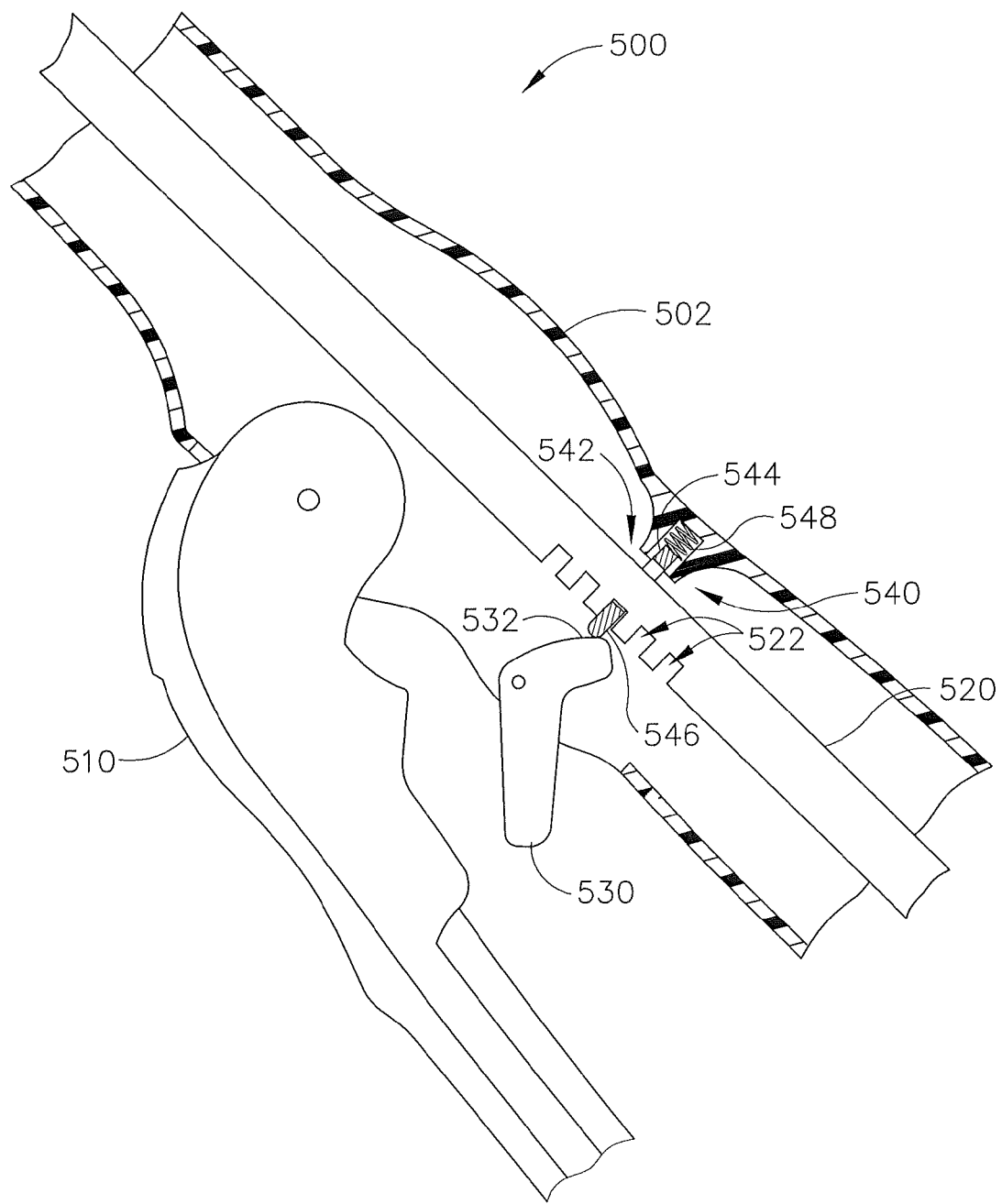
FIG. 10B depicts a partial side cross-sectional view of the trapdoor and lockout feature of FIG. 10A shown in a firing position.

FIGS. 10A-10B depict an exemplary actuator handle assembly (500) for surgical instrument (10), described above, having a body (502), a trigger (510) pivotably mounted to body (502), and a trocar actuator (520) extending longitudinally through body (502). In the present example, trocar actuator (520) is coupled to an anvil (not shown), such as anvil (40), at a distal end. A proximal end of trocar actuator (520) is in communication with an adjusting knob (not shown), such as adjusting knob (98), to actuate trocar actuator (520) proximally and/or distally relative to actuator handle assembly (500). Accordingly, when the anvil is coupled to the distal end of trocar actuator (520) and the adjusting knob is rotated, trocar actuator (520) increases or decreases the distance between the anvil and a stapling head assembly (not shown). Trigger (510) is operable to drive staples (not shown) out of the stapling head assembly and into tissue. Body (502), trigger (510), trocar actuator (520) and/or actuator handle assembly (500) may be further constructed in accordance with at least some of the teachings of body (72), trigger (74), trocar actuator (39), and/or actuator handle assembly (70) described above.

In the example shown, a lockout feature (530) is also pivotably coupled to body (502) and is configured to pivot between a first position shown in FIG. 10A, in which lockout feature (530) is engaged with trigger (510) to substantially prevent trigger (510) from being fired, and a second position shown in FIG. 10B, in which lockout feature (530) is disengaged from trigger (510). Lockout feature (530) may be constructed and/or function at least partially in accordance with lockout feature (82) described above. Lockout feature (530) of this example includes a cam surface (532) configured to engage and actuate a door (540) relative to body (502). In some versions, cam surface (532) may be positioned 90 degrees relative to the main portion of lockout feature (530) such that cam surface (532) does not engage door (540) until lockout feature (530) is pivoted 90 degrees relative to body (502), though this is merely optional. Door (540) comprises a flat plate having an opening (542) through which trocar actuator (520) extends. As shown in FIGS. 10A-10B, door (540) includes a top portion (544) and a bottom portion (546) on opposing sides of opening (542). When door (540) is not actuated by lockout feature (530), top portion (544) abuts a portion of trocar actuator (520) and bottom portion (546) is disengaged from one or more recesses (522) formed in trocar actuator (520), as will be discussed in more detail below. In the present example, a spring (548) is coupled to top portion (544) and body (502) to bias door (540) to the unactuated position shown in FIG. 10A. Bottom portion (546) is sized to enter the one or more recesses (522) when door (540) is actuated by cam surface (532) of lockout feature (530). Of course other constructions for door (540) will be apparent to one of ordinary skill in the art in view of the teachings herein.

Trocar actuator (520) comprises a plurality of lateral recesses (522) formed in trocar actuator (520). By way of example only, recesses (522) are formed in trocar actuator (520) such that recesses (522) are adjacent to bottom portion (546) when trocar actuator (520) and the anvil are in the "green zone." Accordingly, recesses (522) form a plurality of discrete positions where bottom portion (546) can selectively lock trocar actuator (520) when door (540) is actuated by lockout feature (530).

FIG. 10A shows lockout feature (530) in the locked position such that trigger (510) is inoperable by the user. Once the user has rotated the adjusting knob to actuate the anvil (and therefore also trocar actuator (520)) into the "green zone," one or more of the plurality of recesses (522) are positioned adjacent to bottom portion (546) of door (540). When lockout feature (530) is pivoted to the second position, shown in FIG. 10B, cam surface (532) actuates door (540) to push bottom portion (546) into one of the plurality of recesses (522). Thus, if a user inadvertently applies a rotational force on the adjusting knob, door (540) and bottom portion (546) maintains the position of trocar actuator (520) and the anvil relative to the stapling head assembly. With trocar actuator (520) secured relative to body (502) via door (540), the user may then fire the instrument to staple the tissue. Other constructions for trocar actuator (520) and/or door (540) will be apparent to one of ordinary skill in the art in view of the teachings herein.

E. Exemplary Geared Lockout Feature

Figure 11A:
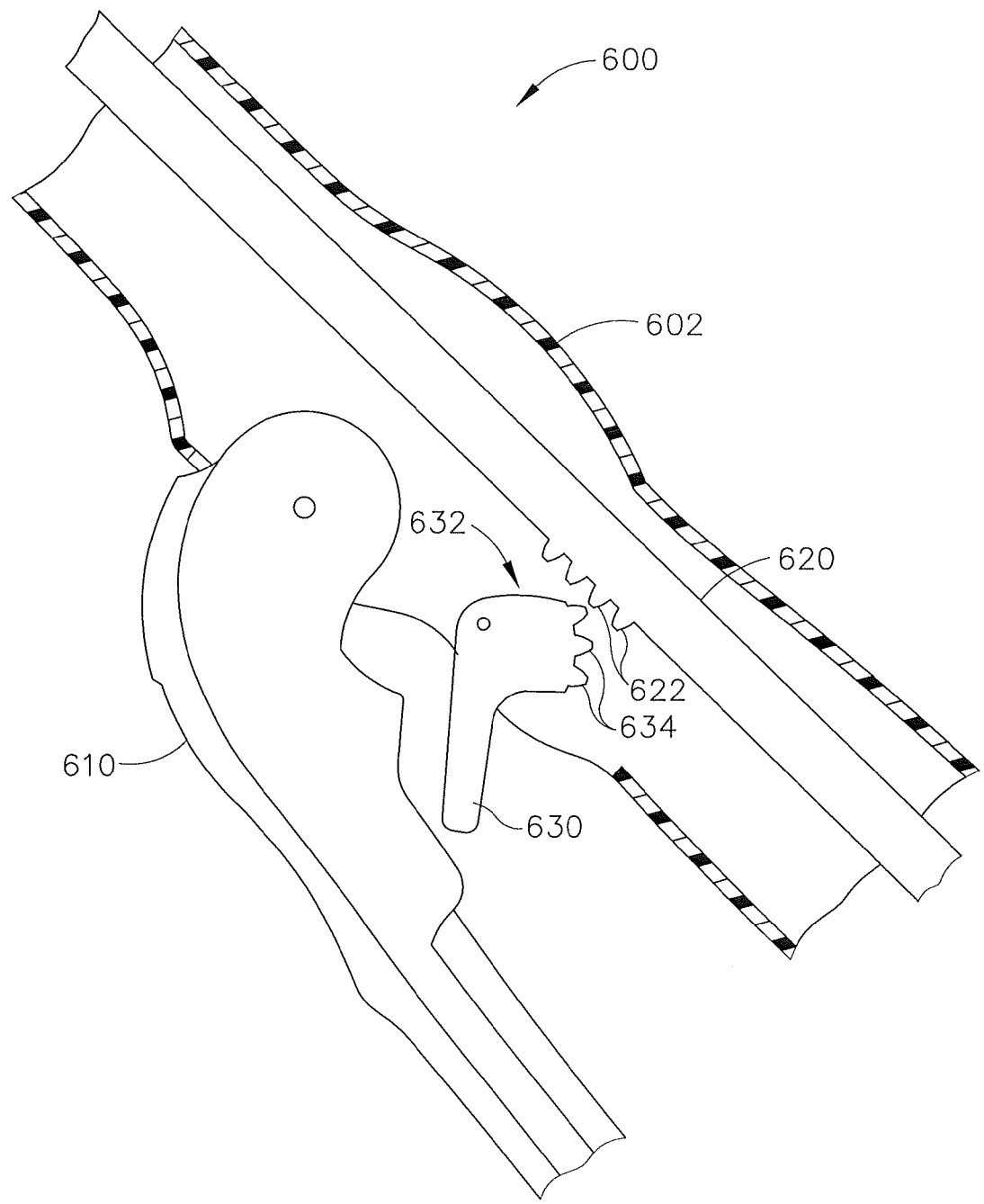
FIG. 11A depicts a partial side cross-sectional view of an exemplary geared lockout feature shown in a locked position.
Figure 11B:
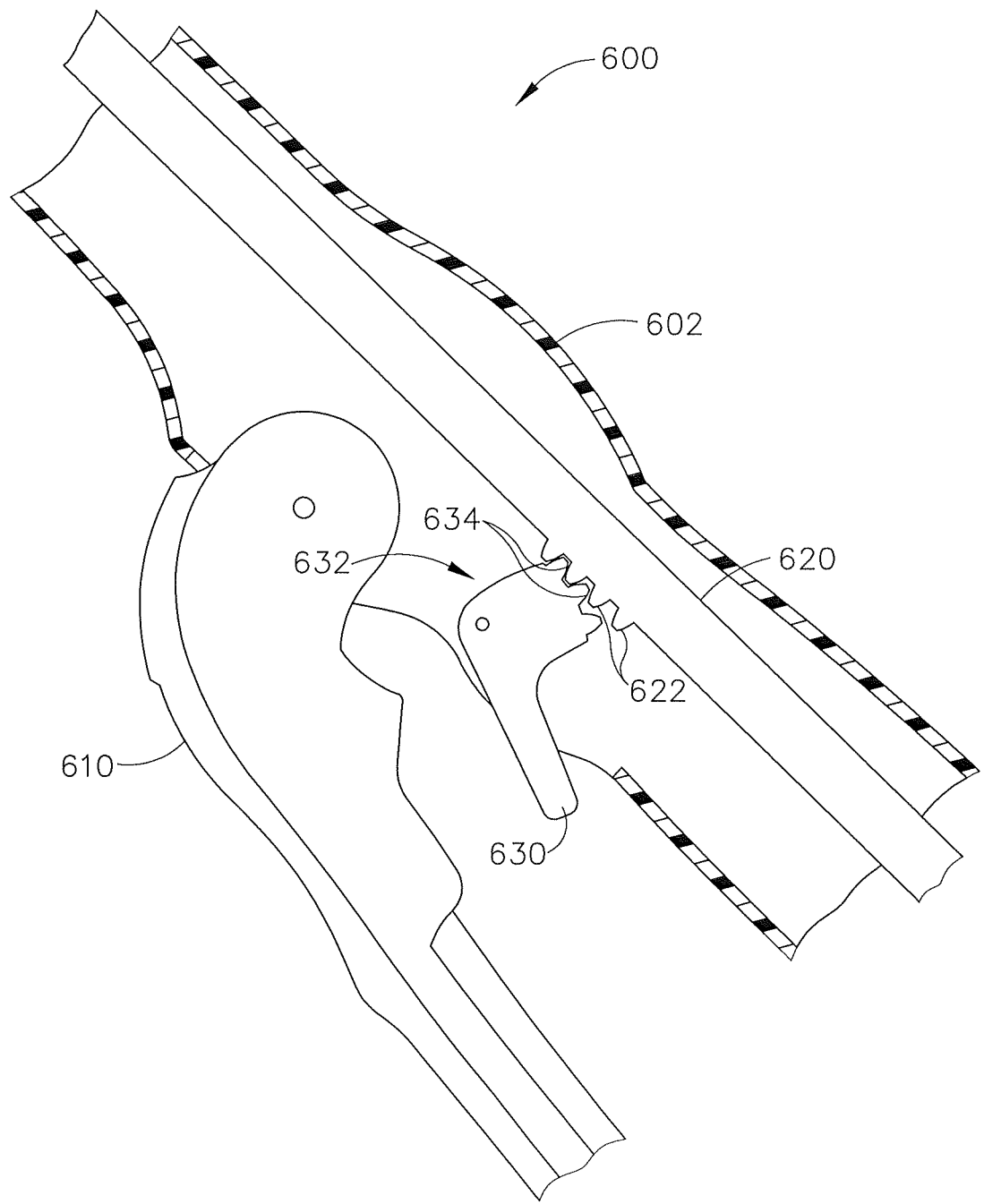
FIG. 11B depicts a partial side cross-sectional view of the geared lockout feature of FIG. 11A shown in a firing position.

FIGS. 11A-11B depict an exemplary actuator handle assembly (600) for surgical instrument (10), described above, having a body (602), a trigger (610) pivotably mounted to body (602), and a trocar actuator (620) extending longitudinally through body (602). In the present example, trocar actuator (620) is coupled to an anvil (not shown), such as anvil (40), at a distal end. A proximal end of trocar actuator (620) is in communication with an adjusting knob (not shown), such as adjusting knob (98), to actuate trocar actuator (620) proximally and/or distally relative to actuator handle assembly (600). Accordingly, when the anvil is coupled to the distal end of trocar actuator (620) and the adjusting knob is rotated, trocar actuator (620) increases or decreases the distance between the anvil and a stapling head assembly (not shown). Trigger (610) is operable to drive staples (not shown) out of the stapling head assembly and into tissue. Body (602), trigger (610), trocar actuator (620) and/or actuator handle assembly (600) may be further constructed in accordance with at least some of the teachings of body (72), trigger (74), trocar actuator (39), and/or actuator handle assembly (70) described above.

In the example shown, a lockout feature (630) is also pivotably coupled to body (602) and is configured to pivot between a first position shown in FIG. 11A, in which lockout feature (630) is engaged with trigger (610) to substantially prevent trigger (610) from being fired, and a second position shown in FIG. 11B, in which lockout feature (630) is disengaged from trigger (610). Lockout feature (630) may be constructed and/or function at least partially in accordance with lockout feature (82) described above. Lockout feature (630) further includes an engagement head (632) having one or more locking members (634), such as gear teeth, configured to engage one or more complementary members (622) on trocar actuator (620). Complementary members (622) are formed in trocar actuator (620) such that complementary members (622) mesh with locking members (634) only when trocar actuator (620) and the anvil are in the "green zone." Accordingly, complementary members (622) form a plurality of discrete positions where locking members (634) can selectively lock trocar actuator (620). Of course complementary members (622) may extend along the entire longitudinal length of trocar actuator (620) or any other portion thereof. By way of example only, locking members (634) comprise three gear teeth that mesh with a plurality of complementary gear teeth on trocar actuator (620). Other meshing members (622, 634) will be apparent to one of ordinary skill in the art in view of the teachings herein. In some versions, locking members (634) of engagement head (632) may be positioned 90 degrees relative to the main portion of lockout feature (630) such that locking members (634) do not engage trocar actuator (620) until lockout feature (630) is pivoted 90 degrees relative to body (602), though this is merely optional. Still further configurations for lockout feature (630) will be apparent to one of ordinary skill in the art in view of the teachings herein.

FIG. 11A shows lockout feature (630) in the locked position such that trigger (610) is inoperable by the user. Once the user has rotated the adjusting knob to actuate the anvil (and therefore also trocar actuator (620)) into the "green zone," one or more of the complementary members (622) are positioned adjacent to engagement head (632) of locking feature (630). When lockout feature (630) is pivoted to the second position, shown in FIG. 11B, locking members (634) of engagement head (632) mesh with complementary members (622). Locking members (634) and complementary members (622) may be sized such that minimal distal movement of trocar actuator (620) occurs when locking members (634) mesh with complementary members (622). In addition, or in the alternative, locking members (634) may comprise resilient ratchet teeth that compress against engagement head (632) when meshing with complementary members (622). The meshing of locking members (634) with complementary members (622) substantially restricts the longitudinal movement of trocar actuator (620). Thus, if a user inadvertently applies a rotational force on the adjusting knob, locking members (634) maintain the position of trocar actuator (620) and the anvil relative to the stapling head assembly. With trocar actuator (620) secured relative to body (602) via members (622, 634), the user may then fire the instrument to staple the tissue. Further configurations for trocar actuator (620) and/or complementary members (622) will be apparent to one of ordinary skill in the art in view of the teachings herein.

F. Exemplary Ratcheted Trocar Actuator Assembly

Figure 12A:
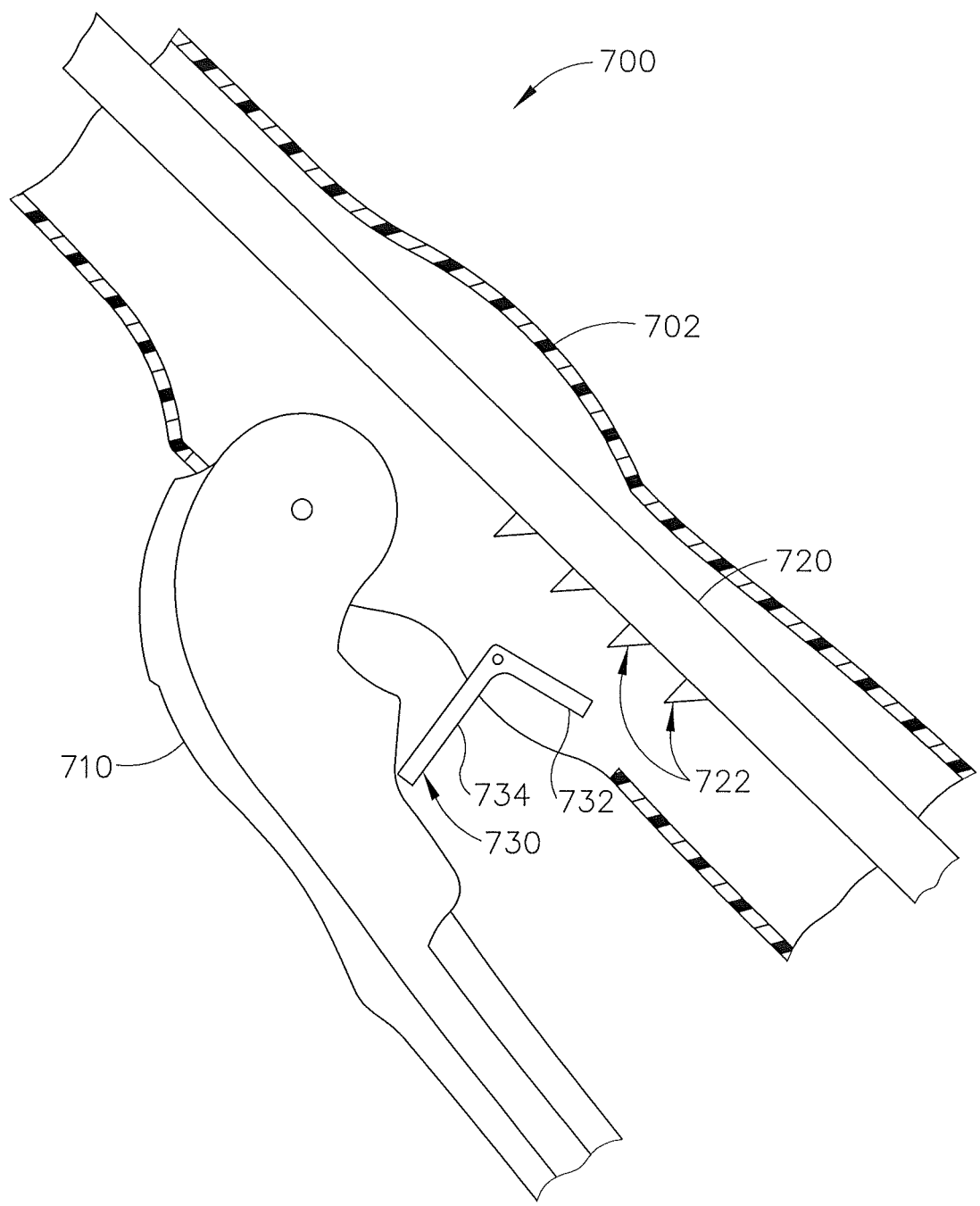
FIG. 12A depicts a partial side cross-sectional view of an exemplary ratcheted trocar actuator and lockout feature shown in a locked position.
Figure 12B:
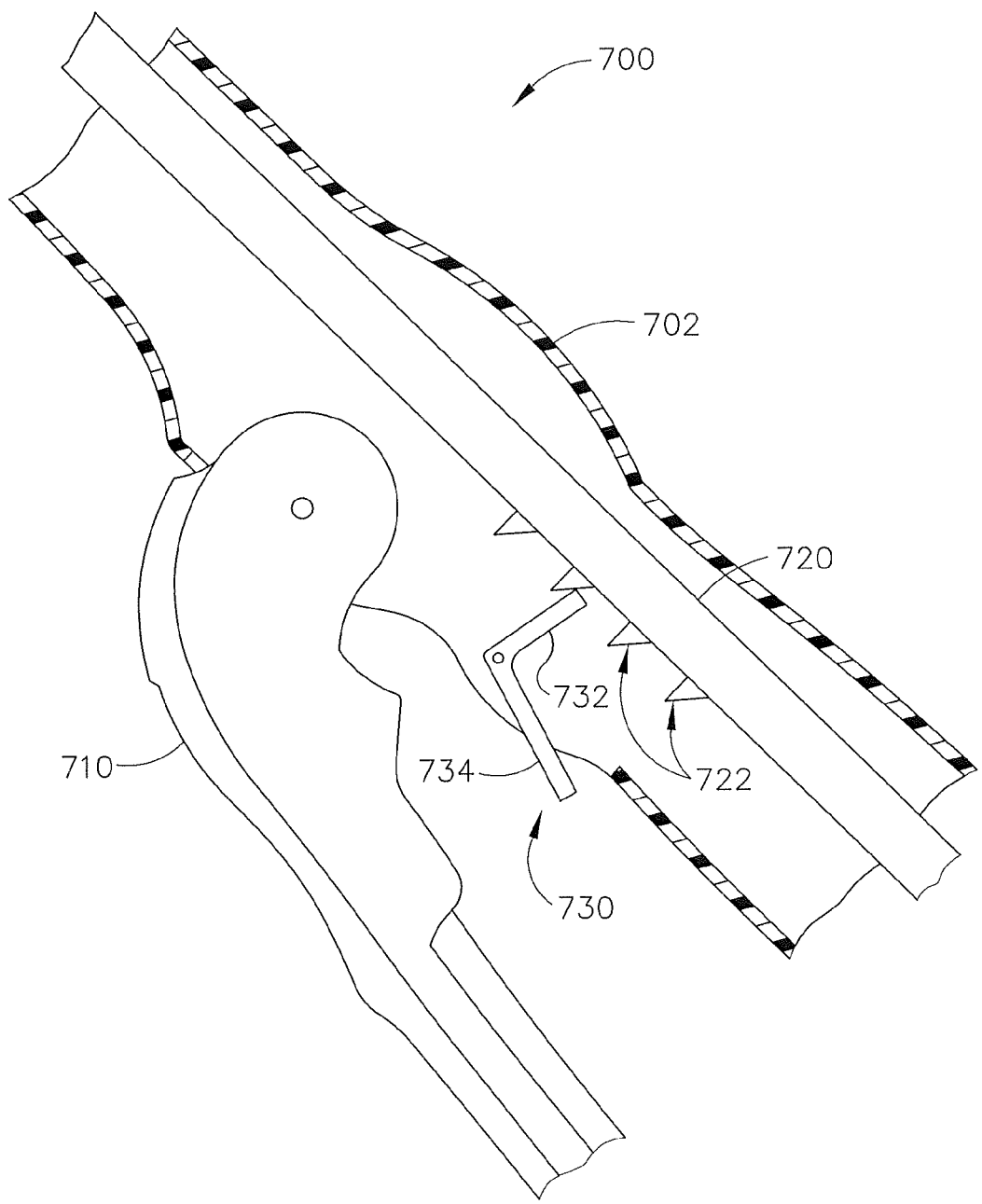
FIG. 12B depicts a partial side cross-sectional view of the ratcheted trocar actuator and lockout feature of FIG. 12A shown in a firing position.

FIGS. 12A-12B depict an exemplary actuator handle assembly (700) for surgical instrument (10), described above, having a body (702), a trigger (710) pivotably mounted to body (702), and a trocar actuator (720) extending longitudinally through body (702). In the present example, trocar actuator (720) is coupled to an anvil (not shown), such as anvil (40), at a distal end. A proximal end of trocar actuator (720) is in communication with an adjusting knob (not shown), such as adjusting knob (98), to actuate trocar actuator (720) proximally and/or distally relative to actuator handle assembly (700). Accordingly, when the anvil is coupled to the distal end of trocar actuator (720) and the adjusting knob is rotated, trocar actuator (720) increases or decreases the distance between the anvil and a stapling head assembly (not shown). Trigger (710) is operable to drive staples (not shown) out of the stapling head assembly and into tissue. Body (702), trigger (710), trocar actuator (720) and/or actuator handle assembly (700) may be further constructed in accordance with at least some of the teachings of body (72), trigger (74), trocar actuator (39), and/or actuator handle assembly (70) described above.

In the example shown, a lockout feature (730) is also pivotably coupled to body (702) and is configured to pivot between a first position shown in FIG. 12A, in which lockout feature (730) is engaged with trigger (710) to substantially prevent trigger (710) from being fired, and a second position shown in FIG. 12B, in which lockout feature (730) is disengaged from trigger (710). Lockout feature (730) may be constructed and/or function at least partially in accordance with lockout feature (82) described above. Lockout feature (730) further includes a catch rod (732) extending from a lever (734) of lockout feature (730). In the present example, catch rod (732) extends perpendicular from lever (734), though this is merely optional. In some versions, catch rod (732) may extend from lever (734) at other angles.

Catch rod (732) is configured to engage and abut one or more ratchet teeth (722) formed on trocar actuator (720). In the present example, ratchet teeth (722) are triangular teeth extending from a side of trocar actuator (720), though this is merely optional. In some versions, ratchet teeth (722) may comprise helical teeth (722) that revolve about trocar actuator (720) to allow catch rod (732) to engage teeth (722) even if trocar actuator (720) is rotated. In an alternative version, ratchet teeth (722) may be annular ledges spaced apart on an outer surface of trocar actuator (720). Moreover, as shown in the present example, ratchet teeth (722) are formed on a portion of trocar actuator (720) that substantially aligns with lockout feature (730), though this is merely optional. Of course still other constructions for ratchet teeth (722) will be apparent to one of ordinary skill in the art in view of the teachings herein.

FIG. 12A shows lockout feature (730) in the locked position such that trigger (710) is inoperable by the user. Once the user has rotated the adjusting knob to actuate the anvil (and therefore also trocar actuator (720)) into the "green zone," ratchet teeth (722) are substantially aligned with locking feature (730). When lockout feature (730) is pivoted to the second position, shown in FIG. 12B, catch rod (732) engages one or more ratchet teeth (722) to prevent trocar actuator (720) from actuating distally relative to body (702). Of course, ratchet teeth (722) permit trocar actuator (720) to actuate proximally relative to body (702). Thus, the user is permitted to further reduce the gap between the anvil and the stapling head assembly, but not increase the gap. With trocar actuator (720) secured relative to body (702) via catch rod (732), the user may then fire the instrument to staple the tissue. Of course other configurations for trocar actuator (720) and/or catch rod (732) will be apparent to one of ordinary skill in the art in view of the teachings herein. For instance, in addition, or in the alternative, catch rod (732) may comprise a flared end that inserts or snaps into a corresponding resilient member formed in trocar actuator (720). In this version, the resilient member may be configured to be a one-way member for catch rod (732) to lock into trocar actuator (720).

G. Exemplary Slotted Trocar Actuator Assembly

Figure 13A:
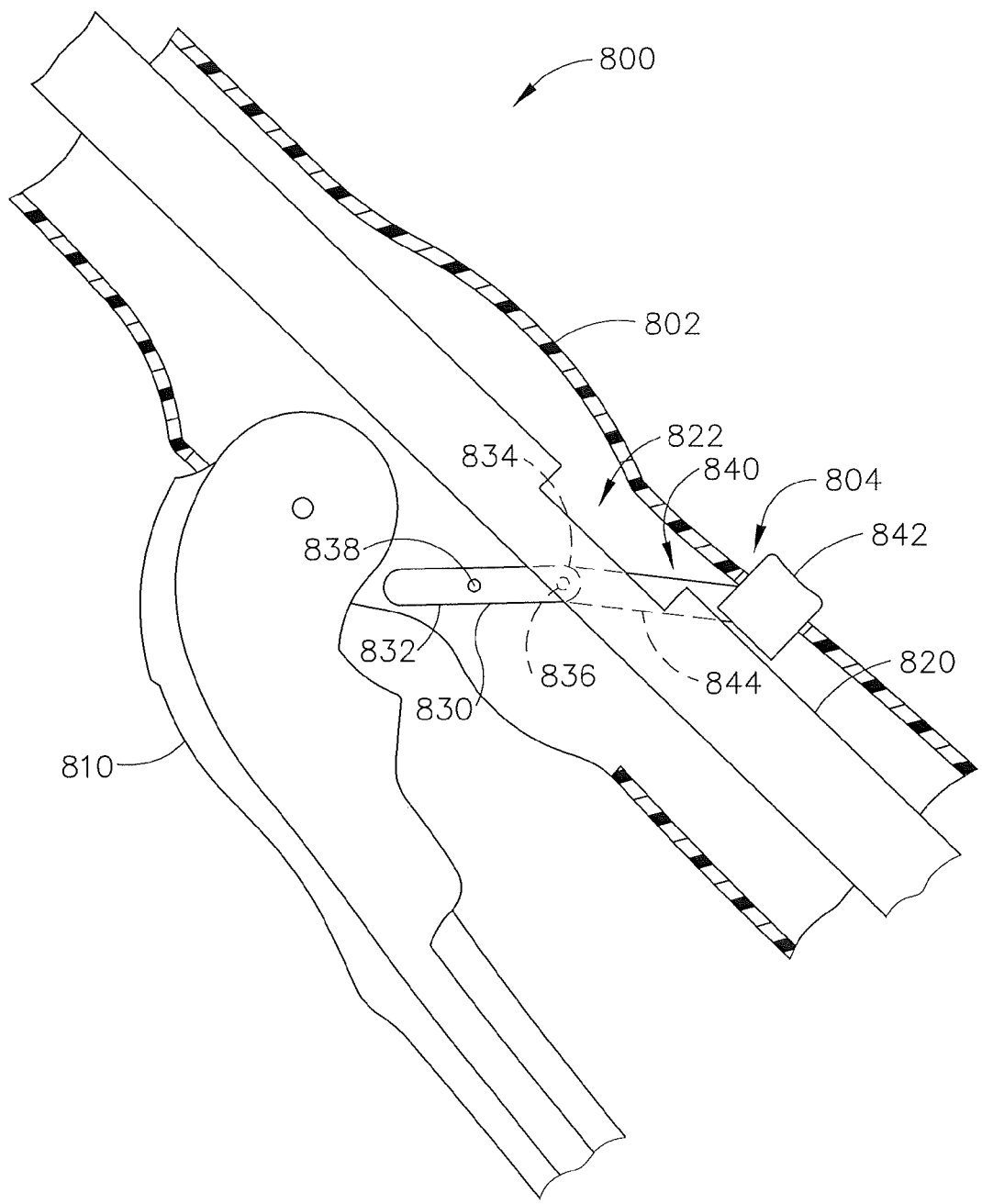
FIG. 13A depicts a partial side cross-sectional view of an exemplary slotted trocar actuator and lockout feature shown in a locked position.
Figure 13B:
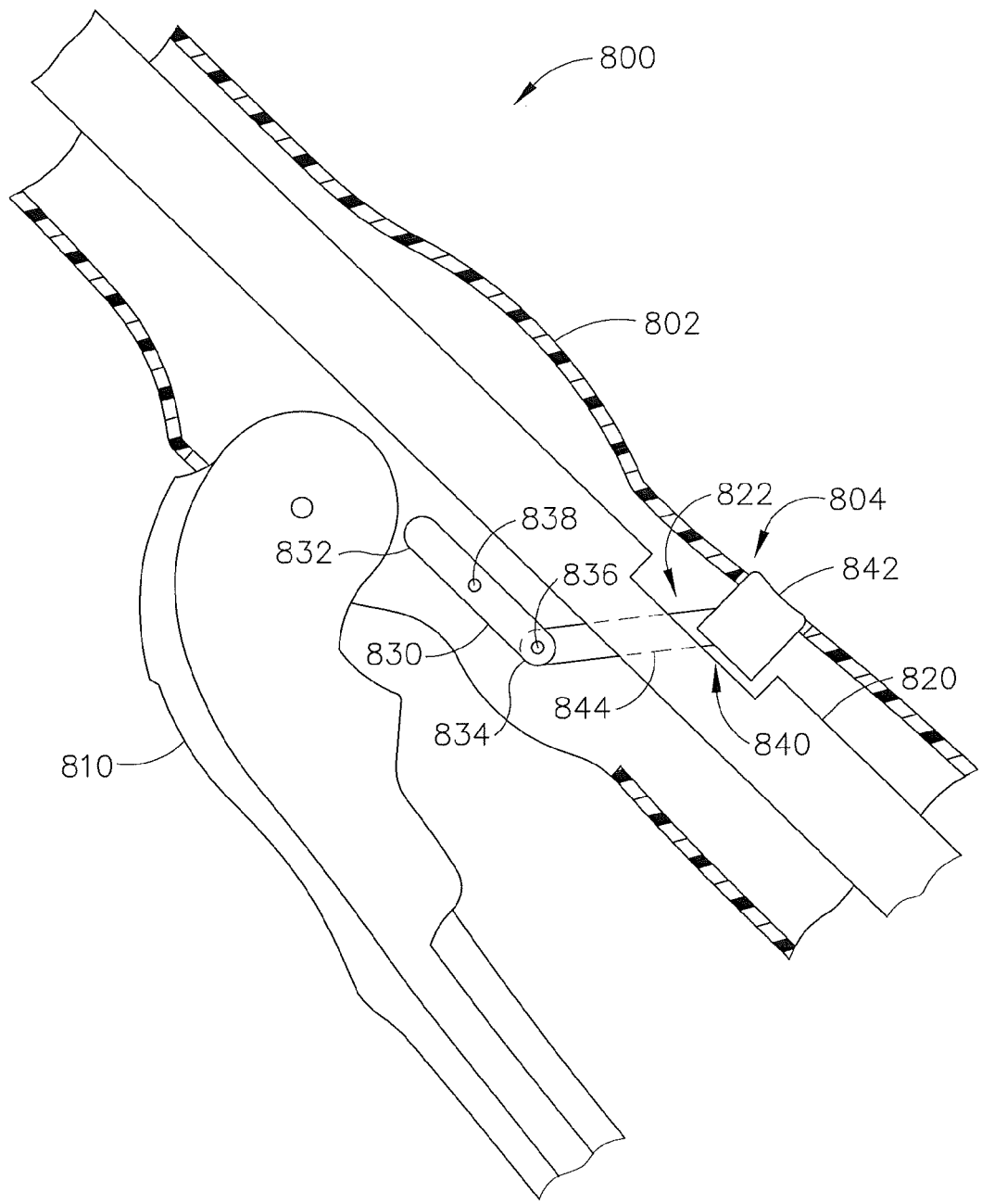
FIG. 13B depicts a partial side cross-sectional view of the slotted trocar actuator and lockout feature of FIG. 13A shown in a firing position.

FIGS. 13A-13B depict an exemplary actuator handle assembly (800) for surgical instrument (10), described above, having a body (802), a trigger (810) pivotably mounted to body (802), and a trocar actuator (820) extending longitudinally through body (802). In the present example, trocar actuator (820) is coupled to an anvil (not shown), such as anvil (40), at a distal end. A proximal end of trocar actuator (820) is in communication with an adjusting knob (not shown), such as adjusting knob (98), to actuate trocar actuator (820) proximally and/or distally relative to actuator handle assembly (800). Accordingly, when the anvil is coupled to the distal end of trocar actuator (820) and the adjusting knob is rotated, trocar actuator (820) increases or decreases the distance between the anvil and a stapling head assembly (not shown). Trigger (810) is operable to drive staples (not shown) out of the stapling head assembly and into tissue. Body (802), trigger (810), trocar actuator (820) and/or actuator handle assembly (800) may be further constructed in accordance with at least some of the teachings of body (72), trigger (74), trocar actuator (39), and/or actuator handle assembly (70) described above.

In the example shown, a lockout feature (830) is also pivotably coupled to body (802) via a pivot point (838) and is configured to pivot between a first position shown in FIG. 13A, in which a first end (832) of lockout feature (830) is engaged with trigger (810) to substantially prevent trigger (810) from being fired, and a second position shown in FIG. 13B, in which first end (832) of lockout feature (830) is disengaged from trigger (810). Lockout feature (830) may be constructed and/or function at least partially in accordance with lockout feature (82) described above. Lockout feature (830) is further pivotably linked to a button assembly (840) at a second end (834) via a pin (836). In the present example, button assembly (840) comprises a button (842) and a rod (844) coupled to button (842). In some versions rod (844) is fixedly coupled to button (842); in others rod (844) is pivotably coupled to button (842). Rod (844) is offset from the vertical plane along which the central axis of trocar actuator (820) extends, such that rod (844) extends downwardly and adjacent to trocar actuator (820). Button (842) is aligned with the vertical plane along which the central axis of trocar actuator (820) extends. Button (842) extends along an axis that is perpendicular of the central axis of trocar actuator (820), through an opening (804) formed in body (802). As depicted in the sequence shown in FIGS. 13A-13B, when button assembly (840) is actuated inwardly, rod (844) pivots second end (834) of lockout feature (830) about pivot point (838) to disengage first end (832) from trigger (810).

Trocar actuator (820) includes a recess (822) configured to receive a portion of button (842) therein. In the present example, recess (822) has a longitudinal length corresponding to the longitudinal path of trocar actuator (820) when actuated within the "green zone" described above. Accordingly, when button (842) is depressed into recess (822), trocar actuator (820) is actuatable within the "green zone," but button (842) abuts an end (824) of recess (822) when either limit of the "green zone" is reached. Of course recess (822) may include a smaller or larger longitudinal length. When trocar actuator (820) is not within the "green zone," button (842) abuts an exterior surface of trocar actuator (820), thereby preventing lockout feature (830) from disengaging from trigger (810).

FIG. 13A shows lockout feature (830) and button assembly (840) in the locked position such that trigger (810) is inoperable by the user. Once the user has rotated the adjusting knob to actuate the anvil (and therefore also trocar actuator (820)) into the "green zone," button (842) is positioned across from at least a portion of recess (822). When button (842) is depressed by the user into recess (822), rod (844) pivots lockout feature (830) to the second position, shown in FIG. 13B. As noted above, the user may then actuate trocar actuator (820), but only within the "green zone." If the user attempts to move trocar actuator (820) out of the "green zone" button (842) impedes the movement of trocar actuator (820) by abutting either end (824) of recess (822). With trocar actuator (820) substantially restricted to movement within the "green zone," the user may then fire the instrument to staple the tissue. Still other constructions for button assembly (840) and/or lockout feature (830) will be apparent to one of ordinary skill in the art in view of the teachings herein. For instance, in some versions, a user may manually or directly pivot lockout feature (830) about pivot point (838) to draw button (842) into recess (822).

III. Exemplary Release Assemblies for Two-Piece Trigger Actuation Assembly

In some instances, it may be useful to a user to only engage trigger actuation assembly (84) when the user is about to fire instrument (10). For instance, trigger actuation assembly (84) may be engaged in response to disengagement of lockout feature (82) and/or positioning of indicator (104) within the "green zone." To accomplish this, for example, one or both of trigger carriage (86) and/or driver actuator (64) may be misaligned or otherwise disengaged to prevent firing when lockout feature (82) is engaged and/or position indicator (104) is outside of the "green zone." Accordingly, various assemblies for disengaging and/or re-engaging trigger actuation assembly (84) for firing will now be described in greater detail.

A. Exemplary Two-Piece Trigger Actuation Assembly Activated by Lockout Feature

Figure 14A:
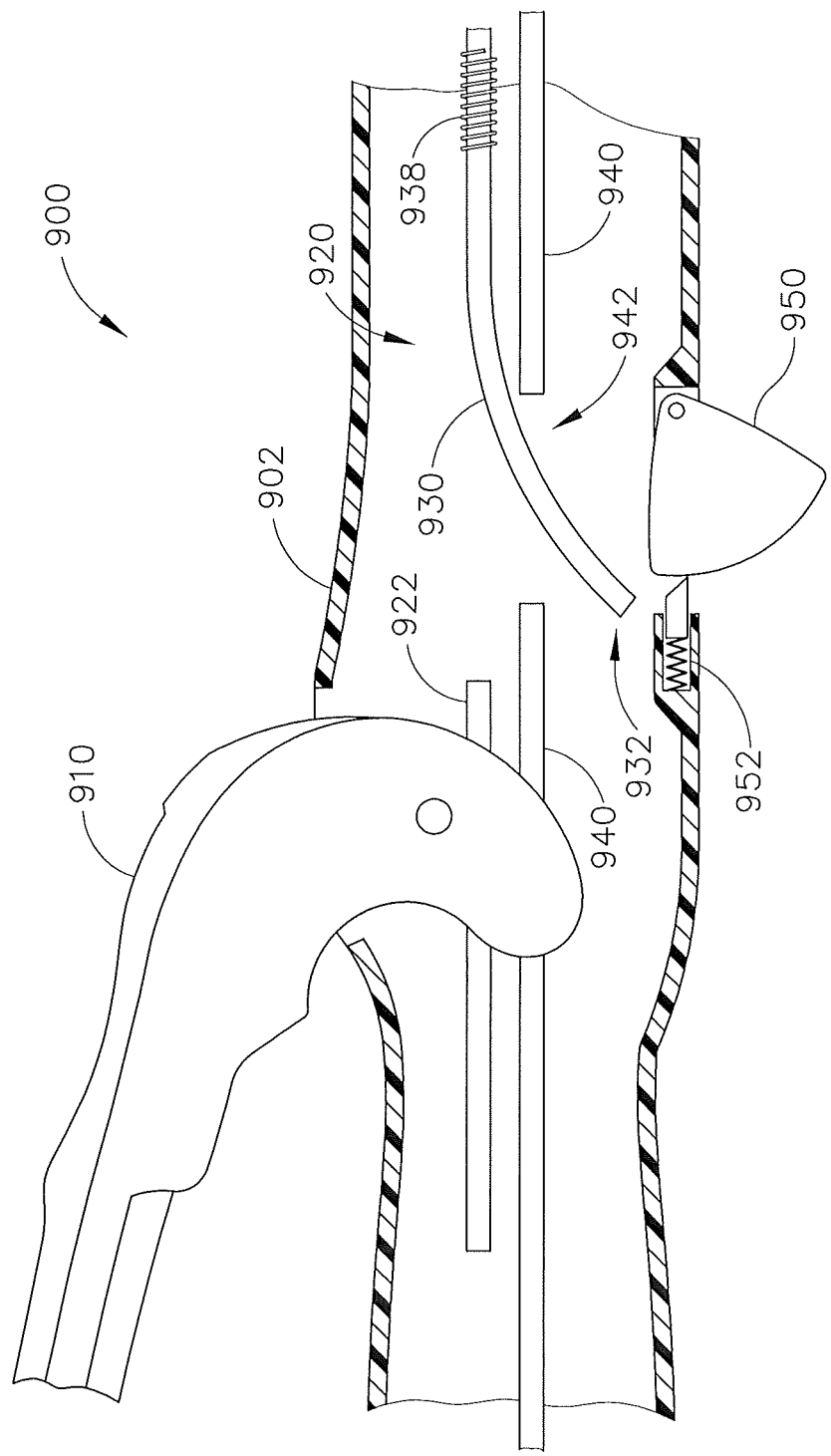
FIG. 14A depicts a partial side cross-sectional view taken along the center of the instrument showing an exemplary two-piece trigger actuation assembly and lockout feature in a locked position.
Figure 14B:
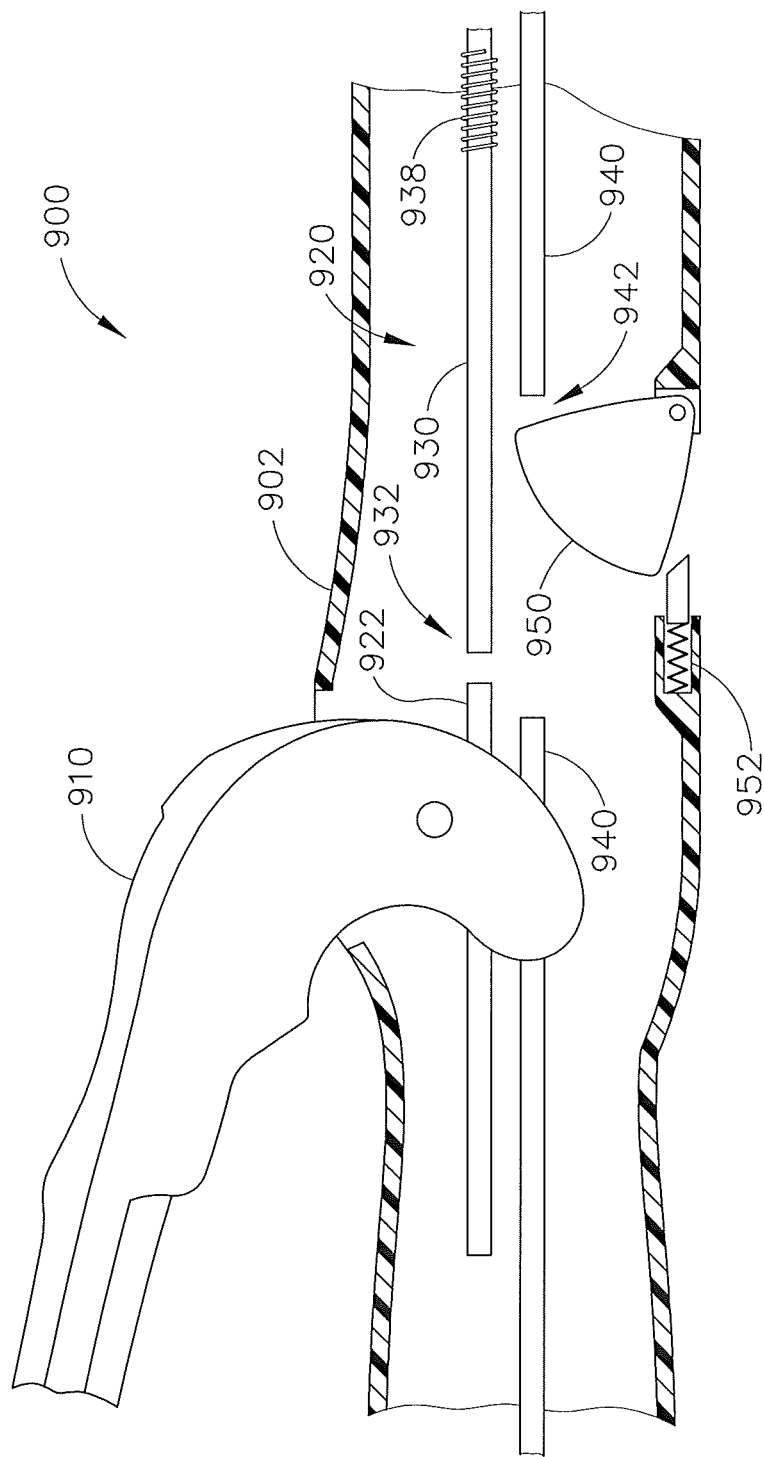
FIG. 14B depicts a partial side cross-sectional view of the two-piece trigger actuation assembly and lockout feature of FIG. 14A shown in a firing position.
Figure 15:
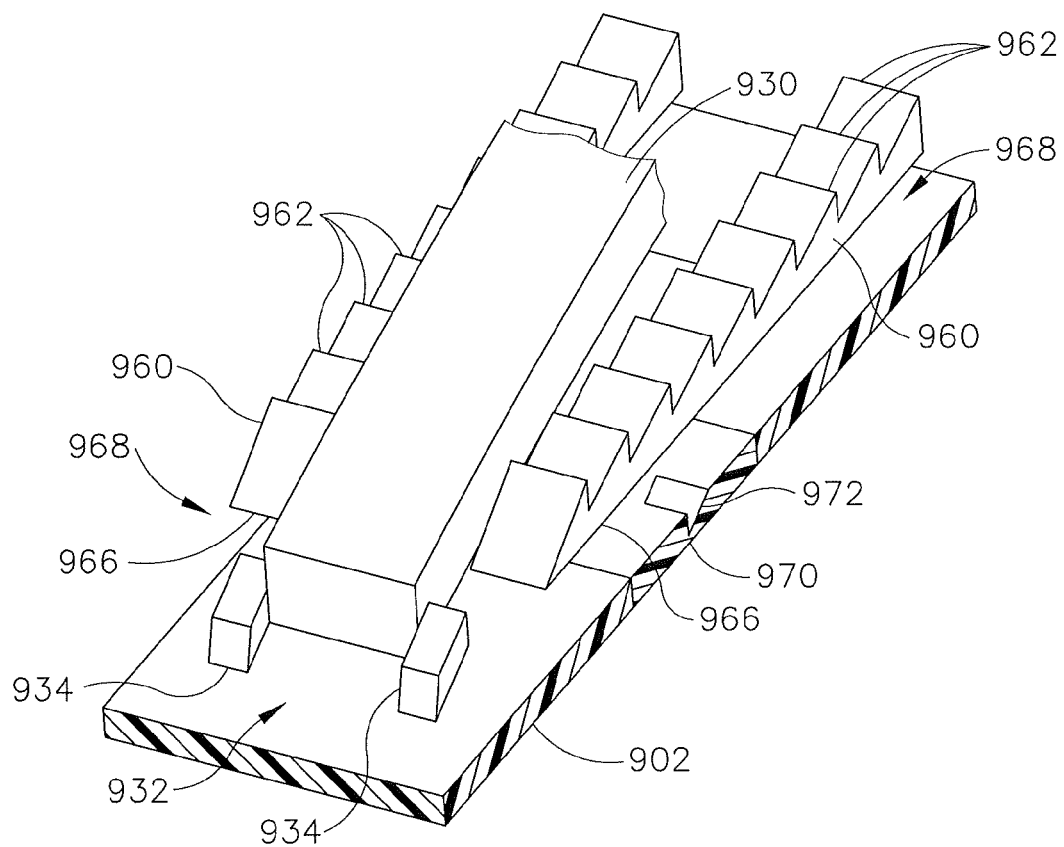
FIG. 15 depicts a partial perspective view of a driver actuator of the two-piece trigger actuation assembly of FIGS. 14A-14B showing a ratchet member and a reset button.

FIGS. 14A-16 depict an exemplary actuator handle assembly (900) for surgical instrument (10), described above, having a body (902), a trigger (910) pivotably mounted to body (902), and a trigger actuation assembly (920). A pair of ratchet members (960), as will be discussed in greater detail below, have been omitted from FIGS. 14A-14B for clarity purposes. In the present example, trigger actuation assembly (920) comprises a trigger carriage member (922) operable to engage and actuate a resilient driver actuator (930). A distal end of driver actuator (930) is coupled to a staple driver (not shown), such as staple driver (24), to drive staples out of a stapling head assembly (not shown), such as stapling head assembly (20). Referring briefly to FIG. 15, a proximal end (932) of driver actuator (930) includes a pair of ratchet teeth (934) that extend outwardly from driver actuator (930) and are configured to engage a corresponding ratchet member (960), as will be described in greater detail below. As shown in FIGS. 14A-16, driver actuator (930) comprises a resilient member biased away from engagement with trigger carriage member (922). In the present example, driver actuator (930) biases away from trigger (910), though this is merely optional. By way of example only, driver actuator (930) comprises a deformable plastic or metallic component that is substantially stiff longitudinally, but bendable laterally. A spring (938) is coupled to driver actuator (930) and urges driver actuator proximally relative to body (902). In some versions, a proximal end of driver actuator (930) may include a recess or other guide features (not shown) configured to receive and guide trigger carriage member (922) into engagement with driver actuator. Driver actuator (930) may be further constructed in accordance with at least some of the teachings of driver actuator (64) described above and/or otherwise, as will be apparent to one of ordinary skill in the art in view of the teachings herein.

Figure 16:
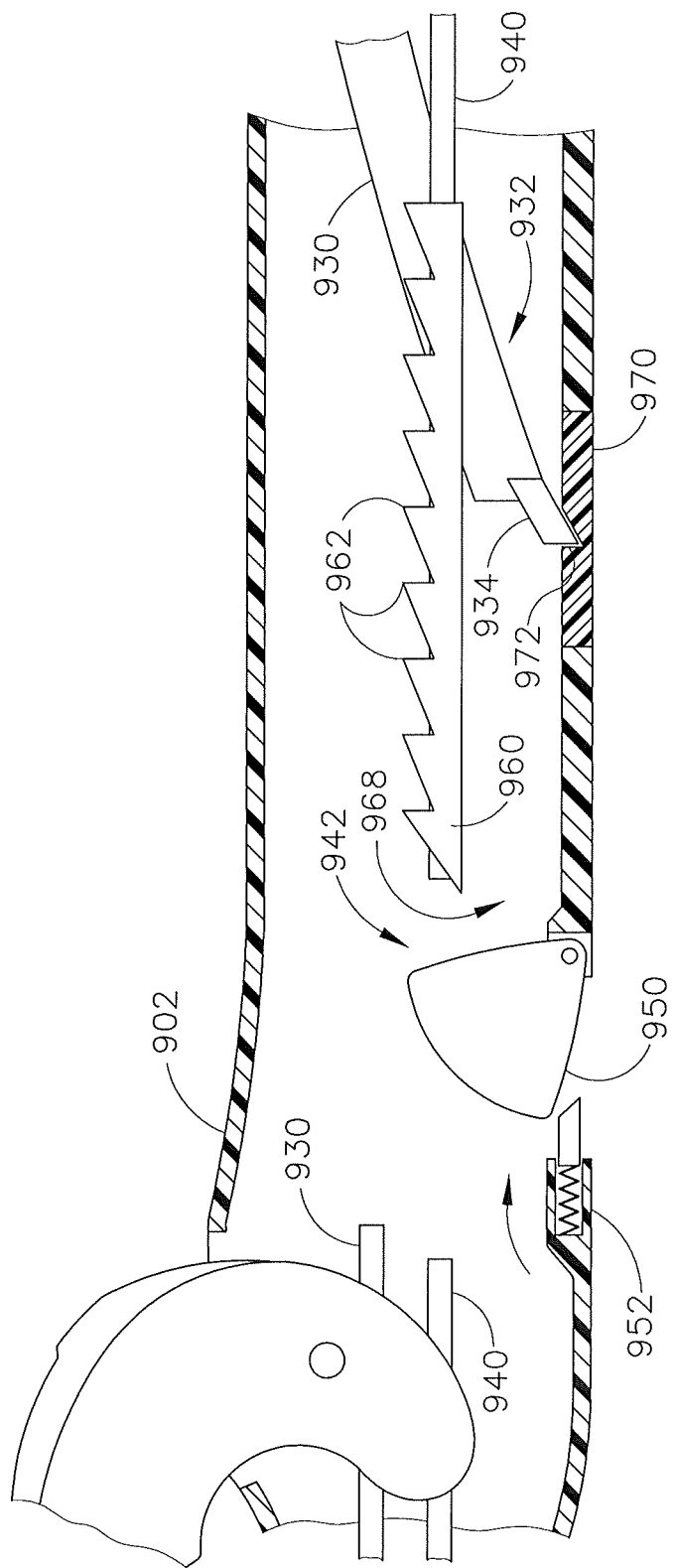
FIG. 16 depicts a side schematic view of the driver actuator, ratchet member, and reset button of FIG. 15, showing driver actuator engaged with reset button.

As noted above, trigger carriage member (922) engages with driver actuator (930), when driver actuator (930) is aligned, and is operable to longitudinally actuate driver actuator (930). As shown in FIGS. 14A-14B and 16, trigger carriage member (922) is engaged with and actuatable by trigger (910). When driver actuator (930) is not longitudinally aligned with trigger carriage member (922), pivoting of trigger (910) actuates trigger carriage member (922), but driver actuator (930) is not driven distally by trigger carriage member (922). Trigger carriage member (922) may be further constructed in accordance with at least some of the teachings of trigger carriage (86) described above and/or in other ways, as will be apparent to one of ordinary skill in the art in view of the teachings herein.

Referring to FIGS. 14A-14B, driver actuator (930) of the present example is biased through an opening (942) formed through an anvil indicator (940). By way of example only, anvil indicator (940) comprises a plate having a longitudinal slot (942) through which driver actuator (930) extends. As shown in FIG. 14A, when anvil indicator (940) is not within the "green zone," anvil indicator (940) impedes driver actuator (930) from being bent into longitudinal alignment with trigger carriage member (922). As shown in FIG. 14B, when anvil indicator (940) indicates that the anvil gap, described above, is within the "green zone," anvil indicator (940) and slot (942) have been actuated proximally to permit driver actuator (930) to be bent into longitudinal alignment with trigger carriage member (922). In an alternative version, driver actuator (930) may comprise a forked end through which anvil indicator (940) extends and a proximal plate impedes driver actuator (930) from bending into alignment with trigger carriage member (922). Anvil indicator (940) may be further constructed in accordance with at least some of the teachings of indicator bracket (140) described above. Of course still further arrangements for anvil indicator (940) will be apparent to one of ordinary skill in the art in view of the teachings herein.

A release (950) is pivotably mounted to body (902) and is operable to bend driver actuator (930) into longitudinal alignment with trigger carriage member (922). Release (950) is pivotable from a first position, shown in FIG. 14A, to a second position, shown in FIG. 14B. In the first position, release (950) is substantially prevented from pivoting by anvil indicator (940) interfering with driver actuator (930). When anvil indicator (940) is actuated to permit driver actuator (930) to pass through slot (942), release (950) is pivotable to the second position, thereby pushing driver actuator (930) into longitudinal alignment with trigger carriage member (922). A spring-loaded latch (952) releasably locks release (950) in the second position to maintain driver actuator (930) in alignment with trigger carriage member (922) prior to operation of trigger (910).

As will be apparent to one of ordinary skill in the art in view of the teachings herein, the disengagement of trigger carriage member (922) from driver actuator (930) and the interference by anvil indicator (940) substantially prevent driver actuator (930) from extending staples and/or the knife from a stapling head assembly, such as stapling head assembly (20) described above, while the anvil is outside of the "green zone." In addition, when release (950) is pivoted into the second position shown in FIG. 14B, release (950) substantially prevents anvil indicator (940) (and therefore an anvil coupled either directly or indirectly to anvil indicator (940)) from being moved outside of the "green zone."

FIGS. 15-16 depict a pair of ratchet members (960) having a plurality of teeth (962) that are configured to provide a ratcheting effect as driver actuator (930) is driven distally via trigger carriage member (922). In the present example, ratchet members (960) extend inwardly from body (902), though this is merely optional and, in some instances, ratchet members (960) may be separate components. A pair of gaps (968) are formed between bottom surfaces (966) of ratchet members (960) and a portion of body (902) such that ratchet teeth (934) may longitudinally translate therethrough. Accordingly, as will be described below, when driver actuator (930) completes a full firing sequence, ratchet teeth (934) pass beyond the distal-most teeth (962) of ratchet members (960) and drop into gaps (968) due to the resilient bias of driver actuator (930). Spring (938) urges driver actuator (930) proximally to translate ratchet teeth (934) proximally through gaps (968).

A pair of detents or notches (972) of a reset button (970) prevent ratchet teeth (934) from translating proximally back to the initial position shown in FIG. 14A. In the present example, reset button (970) comprises a flexible or deformable material, such as rubber or silicone, coupled to body (902) and having notches (972) to receive ratchet teeth (934) therein. Reset button (970) is operable to retain ratchet teeth (934) until a user depresses reset button (970) to release ratchet teeth (934), thereby resetting the instrument to the initial position shown in FIG. 14A. In some versions, latch (952) may be mechanically coupled to a feature (not shown) that is operable to depress or cam reset button (970) when latch (952) is released. Alternatively, reset button (970) may be coupled to latch (952) such that latch (952) releases when reset button (970) is depressed. Accordingly, in such versions, latch (952) and reset button (970) are both simultaneously, or substantially simultaneously, reset to their initial positions. Still other configurations for ratchet members (960) and/or reset button (970) will be apparent to one of ordinary skill in the art in view of the teachings herein.

Referring back to FIG. 14A, trigger (910), trigger carriage member (922), driver actuator (930), anvil indicator (940), and release (950) are shown in an initial position. As noted above, in this position, driver actuator (930) is biased away from longitudinal alignment with trigger carriage member (922) and is prevent from alignment via the interference of a portion of anvil indicator (940). In this position, if the user attempts to fire the device by pivoting trigger (910), trigger carriage member (922) merely translates within the instrument and does not engage driver actuator (930). In addition, or in the alternative, to the assembly described above, a lockout feature (not shown), such as lockout feature (82) described above and/or any of the other lockout features described herein, may be incorporated into the instrument to substantially prevent actuation of trigger (910) prior to the anvil being positioned in the "green zone." Once the user has positioned the anvil such that the anvil gap is within the "green zone," slot (942) is positioned such that driver actuator (930) may pass there through. When the user desires to fire the instrument, the user pivots release (950) to cam driver actuator (930) into longitudinal alignment with trigger carriage member (922) as shown in FIG. 14B. Latch (952) secures release (950) such that driver actuator (930) remains longitudinally aligned with trigger carriage member (922) even if the user is no longer holding release (950) in place. With driver actuator (930) longitudinally aligned with trigger carriage member (922), it should be understood that anvil indicator (940) may be further proximally actuated, but cannot be actuated distally due to interference from driver actuator (930) and/or release (950). Accordingly, this may prevent the instrument from inadvertently moving outside of the "green zone."

To fire the instrument, the user pivots trigger (910) to engage and drive driver actuator (930) distally relative to body (902) and compresses spring (938). As driver actuator (930) is actuated longitudinally, the downward bias of driver actuator (930) (as depicted in FIGS. 14A and 15) engages ratchet teeth (934) with teeth (962) of ratchet members (960) disposed on either side of driver actuator (930). As will be apparent to one of ordinary skill in the art in view of the teachings herein, driver actuator (930) is thus substantially prevented from translating proximally via the engagement of ratchet teeth (934) with teeth (962) (e.g., in the event that the user releases trigger (910) before completing a full firing stroke). Such ratcheting may assist in ensuring that the instrument is fully fired prior to driver actuator (930) resetting to the initial position. Once ratchet teeth (934) extend beyond the distal-most teeth (962), corresponding to a complete firing of the instrument, the resilient bias of driver actuator (930) urges ratchet teeth (934) into gaps (968) and the proximal bias of spring (938) urges driver actuator (930) proximally relative to body (902). As ratchet teeth (934) and driver actuator (930) translate proximally, ratchet teeth (934) catch on notches (972) of reset button (970) shown in FIG. 16. In the present example, the user then releases latch (952) to reset release (950) to the initial position. The user depresses reset button (970) to push ratchet teeth (934) out of notches (972) and spring (938) urges driver actuator (930) back to the initial position shown in FIG. 14A. In versions where latch (952) and reset button (970) are operable at the same time, the user's release of either latch (952) or reset button (970) may also release reset button (970) or latch (952) simultaneously or substantially simultaneously. When driver actuator (930) returns to the initial position, trigger carriage member (922) is again disengaged from driver actuator (930) to permit only a single firing of the instrument each time. The user may then insert new staples and/or a new staple cartridge to fire the instrument again.

While some exemplary configurations for actuator handle assembly (900) having a two-piece trigger actuation assembly (920) have been described, still other configurations will be apparent to one of ordinary skill in the art in view of the teachings herein.

B. Exemplary Two-Piece Trigger Actuation Assembly Activated by Indicator Movement An exemplary alternative actuator handle assembly (1000) for surgical instrument (10), described above, is shown in FIGS. 17A-17B. Actuator handle assembly (1000) comprises a body (1002), a trigger (1010) pivotably mounted to body (1002), and a trigger actuation assembly (1020). In the present example, trigger actuation assembly (1020) comprises a trigger carriage member (1022) operable to engage and actuate a driver actuator (1030). A distal end of driver actuator (1030) is coupled to a staple driver (not shown), such as staple driver (24), to drive staples out of a stapling head assembly (not shown), such as stapling head assembly (20). A proximal end of driver actuator (1030) is coupled or otherwise engaged with trigger carriage member (1022). Driver actuator (1030) may be further constructed in accordance with at least some of the teachings of driver actuator (24) described above.

Figure 17A:
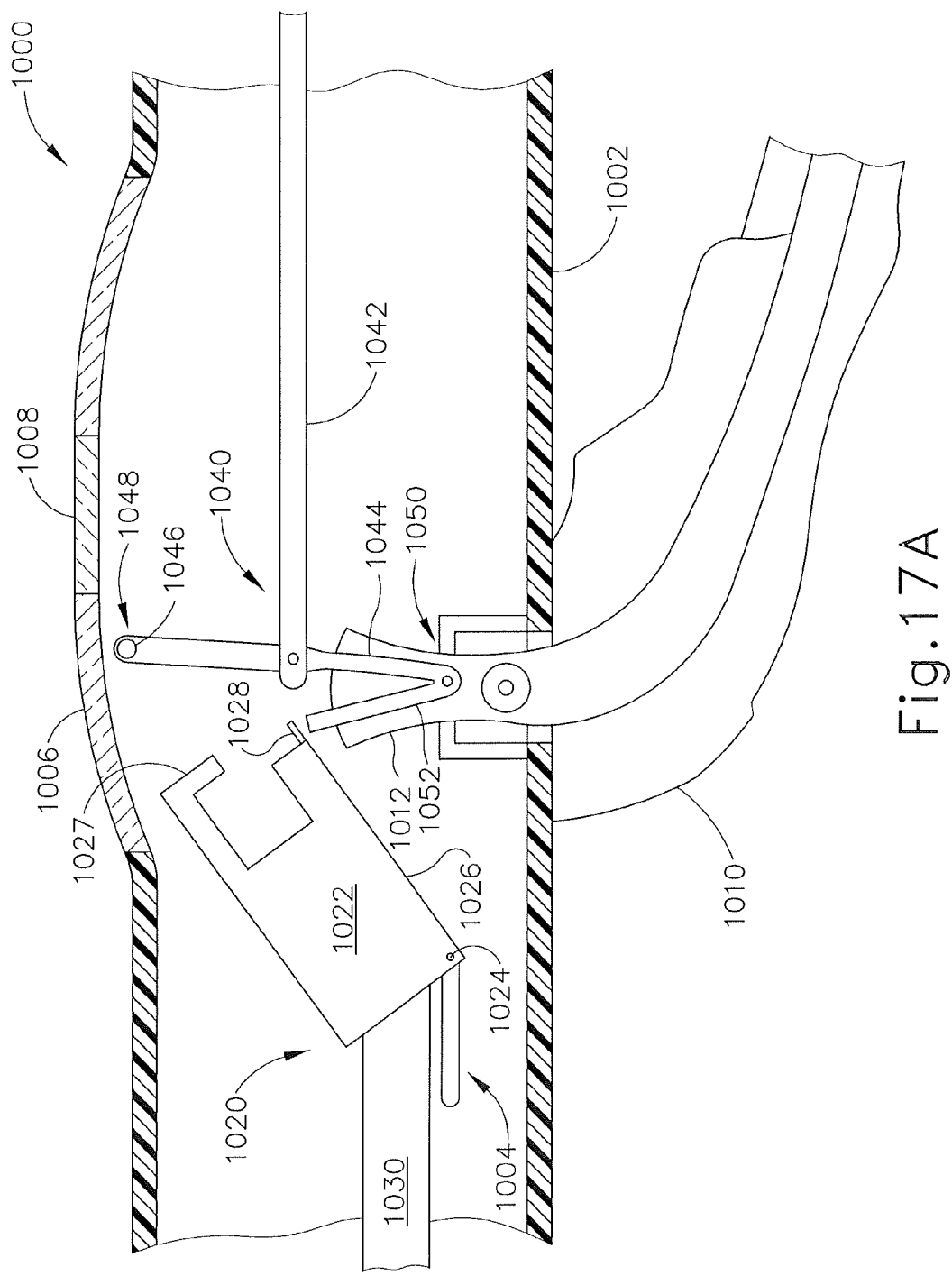
FIG. 17A depicts a partial side cross-sectional view of an exemplary two-piece trigger actuation assembly and exemplary indicator showing a trigger carriage disengaged from a trigger.
Figure 17B:
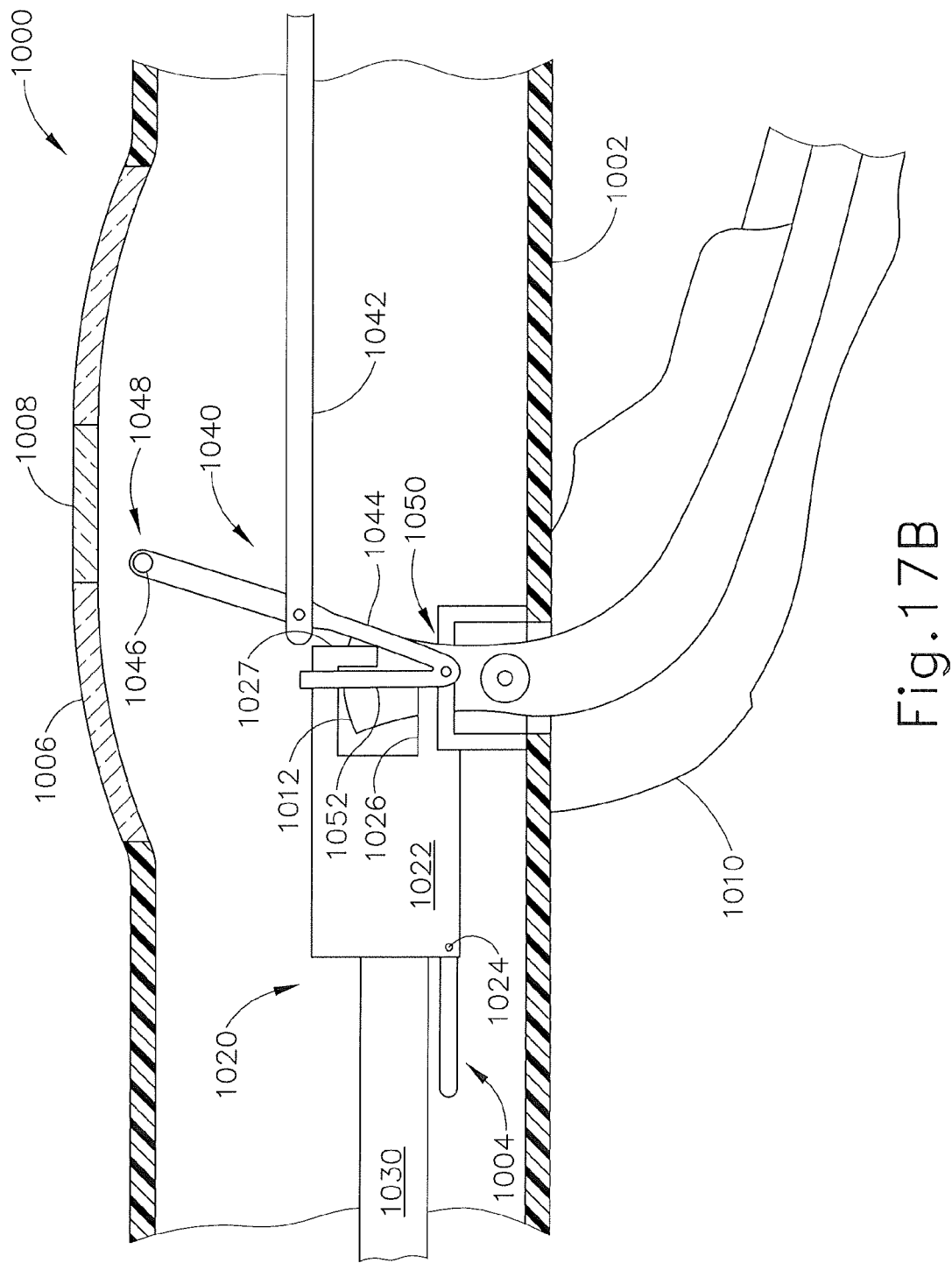
FIG. 17B depicts a partial side cross-sectional view of the trigger actuation assembly of FIG. 17A showing the trigger carriage engaged with the trigger.

As shown in FIG. 17A, trigger carriage member (1022) includes a pair of pivot pins (1024) that extend outwardly from opposing sides of trigger carriage member (1022). Pins (1024) extend into longitudinal channels (1004) formed in body (1002). Thus, pins (1024) permit both rotation about pins (1024) within channels (1004) and longitudinal actuation along channels (1004). Trigger carriage member (1022) also includes a pair of side members (1026) and a rear member (1027) configured to capture and secure an end (1012) of trigger (1010). Accordingly, as seen in FIG. 17B, side members (1026) and rear member (1027) couple to end (1012) of trigger (1010) such that trigger carriage member (1022) is longitudinally actuatable by trigger (1010). A tab (1028) extends from a side member (1026) and is operable to maintain trigger carriage member (1022) in a first position, shown in FIG. 17A. Of course other configurations and/or coupling assemblies for trigger carriage member (1022) and trigger (1010) will be apparent to one of ordinary skill in the art in view of the teachings herein.

An indicator (1040) is pivotally coupled to body (1002) and is operable to indicate the position of an anvil (not shown) relative to a stapling head assembly (not shown) of the instrument through an indicator window (1006) of body (1002). Indicator window (1006) includes a "green zone" region (1008) that indicates when the anvil is in a position corresponding to a preferred operating range of the instrument. In the present example, indicator (1040) is pivotably linked to an actuator (1042) that actuates longitudinally to mechanically link indicator (1040) to the positional movement of the anvil relative to the stapling head assembly. Actuator (1042) and/or indicator (1040) may be constructed and/or assembled in accordance with at least some of the teachings of indicator (104) and/or indicator bracket (140) described above. Indicator (1040) of the present example comprises a V-shaped member having a main portion (1044) with an indicator bar (1046) extending perpendicularly from a first end (1048). Thus, when a user views indicator window (1006), indicator bar (1046) provides a visual indicator of the position of anvil relative to the desired operating range or "green zone." Of course it should be understood that indicator bar (1046) is merely an exemplary component that visually identifies when the instrument is in the "green zone." Other features, such as markings on actuator (1042), may be used to indicate the instrument is in the "green zone" as will be apparent to one of ordinary skill in the art in view of the teachings herein.

A release bracket (1052) extends upwardly and distally relative to main portion (1044) from a second end (1050) of main portion (1044), though this is merely optional. For instance, release bracket (1052) may alternatively be linked to actuator (1042) and/or driver actuator (1030). By way of example only, a cam surface may be provided on actuator (1042) and/or driver actuator (1030) to engage and/or disengage trigger carriage member (1022) and pivot main portion (1044). Alternatively, a window or gap may be provided through actuator (1042) and/or driver actuator (1030) into which a supporting member (not shown) that holds up trigger carriage member (1022) (similar to release bracket (1052)) and enters into the window or gap when actuator (1042) and/or driver actuator (1030) are in a predetermined position for firing. Of course still other features corresponding to the "green zone" may be linked or otherwise coupled to actuator (1042) and/or driver actuator (1030) to engage and/or disengage trigger carriage member (1022) as will be apparent to one of ordinary skill in the art in view of the teachings herein.

As shown in FIG. 17A, an end of release bracket (1052) engages or otherwise supports tab (1028) of trigger carriage member (1022) when indicator (1040) is in an initial position outside of the "green zone." By way of example only, a snap feature may selectively couple release bracket (1052) to tab (1028) such that tab (1028) does not inadvertently disengage from release bracket (1052). Of course other configurations for indicator (1040) will be apparent to one of ordinary skill in the art in light of the teachings herein. For instance, in some versions, release bracket (1052) may be pivotably linked to trigger carriage member (1022). In another configuration, release bracket (1052) may include a cam feature to release trigger carriage member (1022) when indicator (1040) is in the "green zone" and actuates trigger carriage member (1022) upwardly when indicator (1040) is displaced outside of the "green zone." In some versions, the cam feature may be provided on actuator (1042) to cam trigger carriage member (1022) out of engagement with end (1012) of trigger (1010) when actuator (1042) is not in the "green zone." In addition, or in the alternative, a spring (not shown) may be provided to bias trigger carriage member (1022) towards the position shown in FIG. 17A, and the cam feature of actuator (1042) pivots trigger carriage member (1022) into engagement with end (1012). In another version, a spring may be provided to bias trigger carriage member (1022) toward the engaged position shown in FIG. 17B. In such a version, windows or other openings in actuator (1042) are provided to permit passage of trigger carriage member (1022) or other features therethrough only when actuator (1042) is in the "green zone." Thus, when actuator (1042) is not within the "green zone," a portion of actuator (1042) inhibits trigger carriage member (1022) from engaging with trigger (1010). When actuator (1042) is moved out of the "green zone," cammed surfaces on the windows or openings disengage trigger carriage member (1022) from trigger (1010). Of course still other disengagement features will be apparent to one of ordinary skill in the art in view of the teachings herein.

Referring back to FIG. 17A, trigger carriage member (1022) is shown in an initial position angled upwardly and away from engagement with end (1012) of trigger (1010). Release bracket (1052) is engaged with or otherwise supports tab (1028) to maintain trigger carriage member (1022) in this initial position. As also shown, indicator bar (1046) of indicator (1040) is outside of the "green zone" region (1008) in this position. If a user attempts to fire the instrument by pivoting trigger (1010), end (1012) merely pivots within the device and does not engage trigger carriage (1022). As the anvil is positioned within the "green zone" and indicator (1040) pivots via actuator (1042), indicator bar (1046) moves into the "green zone" region (1008), shown in FIG. 17B. Release bracket (1052) is positioned such that release bracket (1052) disengages or no longer supports tab (1028) of trigger carriage member (1022). Trigger carriage member (1022) then pivots about pins (1024) and falls onto end (1012) of trigger (1010) by gravity. Of course a spring (not shown) may be provided to urge trigger carriage member (1022) onto end (1012) as well, though this is merely optional. With trigger carriage member (1022) coupled to trigger (1010), the user may then fire the instrument. Trigger (1010) longitudinally actuates trigger carriage member (1022) along channels (1004) to drive driver actuator (1030) distally to fire staples into tissue. Still further configurations for actuator handle assembly (1000), trigger carriage member (1022), and/or indicator (1040) will be apparent to one of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for stapling tissue comprising:
   (a) a body;
   (b) a trigger pivotably mounted to the body;

(c) an actuator extending longitudinally within the body and operable to actuate longitudinally therein;

(d) a lockout member pivotably mounted to the body, wherein the lockout member is pivotable from a first position, in which the lockout member is engaged with the trigger, to a second position, in which the lockout member is disengaged from the trigger; and (e) a securing feature associated with the lockout member and the actuator, wherein the securing feature is configured to translate axially in response to pivoting of the lockout member, wherein the securing feature is operable to restrict the longitudinal actuation of the actuator when the lockout member is in the second position.

2. The apparatus of claim 1 wherein the securing feature comprises a brake having an engagement tab, wherein the actuator comprises a longitudinal slot, wherein the lockout member is operable to cam the brake such that the engagement tab inserts into the slot when the lockout member is pivoted to the second position.

3. The apparatus of claim 2 wherein the actuator is operable to actuate longitudinally along a predetermined range while the engagement tab is inserted therein.

4. The apparatus of claim 1 wherein the securing feature comprises a lock, wherein the lockout member is operable to engage the lock with the actuator when the lockout member is pivoted to the second position.

5. The apparatus of claim 4 wherein the lock comprises an edge, wherein the edge comprises a friction material that resists longitudinal actuation of the actuator.

6. The apparatus of claim 4 wherein the lock comprises an edge, wherein the actuator comprises a plurality of teeth disposed on an exterior surface of the actuator, wherein the edge engages the teeth when the lockout member is pivoted to the second position.

7. The apparatus of claim 1 wherein the securing feature comprises a cam surface of the lockout member, wherein the cam surface comprises a friction material that resists longitudinal actuation of the actuator when the lockout member is pivoted to the second position.

8. The apparatus of claim 1 wherein the securing feature comprises an actuatable door, wherein the door comprises an opening through which the actuator extends, wherein the actuator comprises one or more recesses, wherein a portion of the door engages the one or more recesses of the actuator when the lockout member is pivoted to the second position.

9. The apparatus of claim 8 wherein the door is coupled to a spring, wherein the spring biases the door such that the portion of the door is disengaged from the one or more recesses.

10. The apparatus of claim 1 wherein the securing feature comprises a plurality of teeth disposed about a portion of the lockout member, wherein the actuator comprises one or more teeth complementary to the teeth of the lockout member.

11. The apparatus of claim 1 wherein the securing feature comprises one or more ratchet teeth disposed on an outer surface of the actuator, wherein the lockout member comprises a catch rod operable to engage the one or more ratchet teeth when the lockout member is pivoted to the second position.

12. The apparatus of claim 11 wherein the one or more ratchet teeth comprise helical ledges disposed on the outer surface of the actuator.

13. The apparatus of claim 11 wherein the one or more ratchet teeth comprise a plurality of annular ledges disposed on the outer surface of the actuator.

14. The apparatus of claim 1 wherein the securing feature comprises a button assembly, wherein the actuator comprises a longitudinal recess sized to receive a button of the button assembly, and wherein the button assembly is operable to pivot the lockout member to the second position when the button is actuated into the recess of the actuator.

15. The apparatus of claim 1 further comprising:
(a) a stapling head assembly coupled to a distal end of the body, wherein the trigger is operable to activate the stapling head assembly; and
(b) an anvil selectively coupleable to a distal end of the actuator;
wherein the actuator is operable to longitudinally actuate the anvil relative to the stapling head assembly.

16. An apparatus for stapling tissue comprising:
(a) a body;
(b) a stapling head assembly coupled to a distal end of the body, wherein the stapling head assembly is operable to drive staples distally relative to the body;
(c) an actuator extending longitudinally along a longitudinal axis through the body and stapling head assembly, wherein the actuator is configured to translate along the longitudinal axis;
(d) an anvil selectively coupleable to the actuator;
(e) a lockout member pivotably mounted to the body; and
(f) a securing feature associated with the lockout member and the actuator, wherein the securing feature is configured to translate transversely relative to the longitudinal axis in response to pivotal movement of the lockout member relative to the body in order to selectively longitudinally secure the actuator relative to the body.

17. An apparatus for stapling tissue comprising:
(a) a body;
(b) a trigger pivotably mounted to the body;
(c) an actuator extending longitudinally within the body and operable to actuate longitudinally therein;
(d) a lockout member pivotably mounted to the body, wherein the lockout member is pivotable from a first position, in which the lockout member is configured to prevent firing of the trigger, to a second position, in which the lockout member is configured to allow firing of the trigger; and
(e) a securing feature associated with the lockout member and the actuator, wherein the securing feature is operable to restrict the longitudinal actuation of the actuator, wherein the securing feature is operable to translate transversely relative to the actuator to engage or disengage the actuator in response to the lockout member pivoting.

* * * * *

UNITED STATES PATENT AND TRADEMARK OFFICE
CERTIFICATE OF CORRECTION

PATENT NO.        : 9,603,599 B2                                             Page 1 of 1
APPLICATION NO.   : 13/328344
DATED             : March 28, 2017
INVENTOR(S)       : Miller et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1279 days.

Signed and Sealed this
Twenty-fifth Day of September, 2018

Andrei Iancu
*Director of the United States Patent and Trademark Office*